(12) United States Patent
Banfalvi

(10) Patent No.: US 9,610,088 B2
(45) Date of Patent: *Apr. 4, 2017

(54) MANIPULATOR FOR GRASPING TISSUE

(71) Applicant: MITEAS LTD., Providence, Mahe (SC)

(72) Inventor: Peter Ferenc Banfalvi, Mor (HU)

(73) Assignee: A-BASE KORLATOLT FELELOSSEGU TARSASAG, Mor (HU)

( * ) Notice: Subject to any disclaimer, the term of this patent is extended or adjusted under 35 U.S.C. 154(b) by 61 days.

This patent is subject to a terminal disclaimer.

(21) Appl. No.: 14/675,897

(22) Filed: Apr. 1, 2015

(65) Prior Publication Data

US 2015/0216544 A1 Aug. 6, 2015

Related U.S. Application Data

(63) Continuation of application No. 13/449,190, filed on Apr. 17, 2012, now Pat. No. 9,265,514.

(51) Int. Cl.
*A61B 18/18* (2006.01)
*A61B 17/28* (2006.01)
(Continued)

(52) U.S. Cl.
CPC ........ *A61B 17/2812* (2013.01); *A61B 17/282* (2013.01); *A61B 17/2816* (2013.01);
(Continued)

(58) Field of Classification Search
CPC . A61B 18/1442; A61B 18/1445; A61B 17/28; A61B 17/2804; A61B 17/2812;
(Continued)

(56) References Cited

U.S. PATENT DOCUMENTS 872,217 A 11/1907 Bonesteel
1,659,112 A 2/1928 Littlejohn
(Continued)

FOREIGN PATENT DOCUMENTS

EP 0449663 10/1991

OTHER PUBLICATIONS

M. A. Van Veelan, Surg Endosc. Jan. 2002;16(1):201-7. Epub Nov. 12, 2001. "Improved usability of a new handle design for laparoscopic dissection forceps", pp. 201-207.
(Continued)

*Primary Examiner* — Edward Moran
*Assistant Examiner* — Elizabeth K So
(74) *Attorney, Agent, or Firm* — Tucker Ellis LLP

(57) ABSTRACT

A manipulator adapted to grasp and draw tissue comprises first and second arms having proximal ends and distal ends separated by a distance. First and second grasping surfaces each connected to and extending from respective distal ends of the first and second arms are biased toward each other by a respective spring force. When the first and second arms are actuated to reduce the distance, the manipulator is configured such that tissue arranged between the first and second grasping surfaces resist actuation of the first and second arms. The first and second arms are further actuatable to overcome the spring force of the first and second grasping surfaces so that the first and second grasping surfaces pivot at respective pivot points such that the distance between the distal ends of the first and second arms is reduced.

5 Claims, 32 Drawing Sheets

(51) Int. Cl.
*A61B 17/29* (2006.01)
*A61B 17/00* (2006.01)

(52) U.S. Cl.
CPC ..... *A61B 17/29* (2013.01); *A61B 2017/00473* (2013.01); *A61B 2017/2829* (2013.01); *A61B 2017/2915* (2013.01); *A61B 2017/2926* (2013.01); *A61B 2017/2945* (2013.01)

(58) Field of Classification Search
CPC .............. A61B 17/2816; A61B 17/282; A61B 17/2833; A61B 17/2841; A61B 17/2909; A61B 2017/2926; A61B 2017/2627; A61B 2017/2929; A61B 2017/293; A61B 2017/2931; A61B 2017/2932; A61B 2017/2933; A61B 2017/2934; A61B 2017/2936; A61B 2017/2937; A61B 2017/2938; A61B 2017/2939; A61B 2017/294; A61B 2017/2941; A61B 2017/2943; A61B 2017/2944; A61B 2017/2945; A61B 18/1443; A61B 18/1444; A61B 18/1446; A61B 2017/2915; A61B 17/29; A61B 17/2903; A61B 2017/2901; A61B 2017/2904; A61B 2017/2913; A61B 2017/2919; A61B 2017/2947

See application file for complete search history.

(56) References Cited

U.S. PATENT DOCUMENTS

| | | |
|---|---|---|
| 1,878,671 A | 9/1932 | Cantor |
| 2,067,031 A | 1/1937 | Wappler |
| 2,201,610 A | 5/1940 | Dawson, Jr. |
| 2,413,142 A | 12/1946 | Jones et al. |
| 2,510,198 A | 6/1950 | Tesmer |
| 2,533,494 A | 12/1950 | Mitchell, Jr. |
| 2,668,538 A | 2/1954 | Baker |
| 2,723,666 A | 11/1955 | Greenberg |
| 2,890,519 A | 6/1959 | Storz, Jr. |
| 3,060,972 A | 10/1962 | Sheldon |
| 3,096,962 A | 7/1963 | Meijs |
| 3,150,379 A | 9/1964 | Brown |
| 3,162,214 A | 12/1964 | Bazinet, Jr. |
| 3,166,072 A | 1/1965 | Sullivan, Jr. |
| 3,168,274 A | 2/1965 | Street |
| 3,190,286 A | 6/1965 | Stokes |
| 3,266,059 A | 8/1966 | Stelle |
| 3,430,662 A | 3/1969 | Guarnaschelli |
| 3,494,006 A | 2/1970 | Brumlik |
| 3,517,128 A | 6/1970 | Hines |
| 3,546,961 A | 12/1970 | Marton |
| 3,551,987 A | 1/1971 | Wilkinson |
| 3,579,751 A | 5/1971 | Jonckheere |
| 3,583,393 A | 6/1971 | Takahashi |
| 3,643,653 A | 2/1972 | Takahashi et al. |
| 3,646,615 A | 3/1972 | Ness |
| 3,664,345 A | 5/1972 | Dabbs et al. |
| 3,665,926 A | 5/1972 | Flores |
| 3,750,652 A | 8/1973 | Sherwin |
| 3,753,438 A | 8/1973 | Wood et al. |
| 3,827,277 A | 8/1974 | Weston |
| 3,835,841 A | 9/1974 | Terada |
| 3,857,395 A | 12/1974 | Johnson et al. |
| 3,858,578 A | 1/1975 | Milo |
| 3,867,944 A | 2/1975 | Samuels |
| 3,871,379 A | 3/1975 | Clarke |
| 3,874,388 A | 4/1975 | King et al. |
| 3,877,434 A | 4/1975 | Ferguson et al. |
| 3,897,775 A | 8/1975 | Furihata |
| 3,910,281 A | 10/1975 | Kletschka et al. |
| 3,913,565 A | 10/1975 | Kawahara |
| 3,915,157 A | 10/1975 | Mitsui |
| 3,948,251 A | 4/1976 | Hosono |
| 3,958,576 A | 5/1976 | Komiya |
| 3,974,834 A | 8/1976 | Kane |
| 3,976,079 A | 8/1976 | Samuels et al. |
| 4,006,747 A | 2/1977 | Kronenthal et al. |
| 4,007,743 A | 2/1977 | Blake |
| 4,036,218 A | 7/1977 | Yamashita et al. |
| 4,038,987 A | 8/1977 | Komiya |
| 4,054,128 A | 10/1977 | Seufert et al. |
| 4,060,089 A | 11/1977 | Noiles |
| 4,069,825 A | 1/1978 | Akiyama |
| 4,177,813 A | 12/1979 | Miller et al. |
| 4,201,198 A | 5/1980 | Okada et al. |
| 4,224,929 A | 9/1980 | Furihata |
| 4,235,238 A | 11/1980 | Ogiu et al. |
| 4,245,624 A | 1/1981 | Komiya |
| 4,246,698 A | 1/1981 | Lasner et al. |
| 4,271,838 A | 6/1981 | Lasner et al. |
| 4,274,415 A | 6/1981 | Kanamoto et al. |
| 4,366,810 A | 1/1983 | Slanetz, Jr. |
| 4,367,746 A | 1/1983 | Derechinsky |
| 4,414,720 A | 11/1983 | Crooms |
| 4,462,402 A | 7/1984 | Burgio et al. |
| 4,494,531 A | 1/1985 | Gianturco |
| 4,532,926 A | 8/1985 | O'Holla |
| 4,534,350 A | 8/1985 | Golden et al. |
| 4,548,202 A | 10/1985 | Duncan |
| 4,586,502 A | 5/1986 | Bedi et al. |
| 4,586,503 A | 5/1986 | Kirsch et al. |
| 4,590,938 A | 5/1986 | Segura et al. |
| 4,592,339 A | 6/1986 | Kuzmak et al. |
| 4,592,356 A | 6/1986 | Gutierrez |
| 4,595,007 A | 6/1986 | Mericle |
| 4,602,631 A | 7/1986 | Funatsu |
| 4,610,250 A | 9/1986 | Green |
| 4,625,726 A | 12/1986 | Duthoy |
| 4,648,733 A | 3/1987 | Merkt |
| 4,651,718 A | 3/1987 | Collins et al. |
| 4,654,028 A | 3/1987 | Suma |
| 4,655,219 A | 4/1987 | Petruzzi |
| 4,655,257 A | 4/1987 | Iwashita |
| 4,669,473 A | 6/1987 | Richards et al. |
| 4,671,278 A | 6/1987 | Chin |
| 4,700,693 A | 10/1987 | Lia et al. |
| 4,705,040 A | 11/1987 | Mueller et al. |
| 4,705,041 A | 11/1987 | Kim |
| 4,711,002 A | 12/1987 | Kreeger |
| 4,724,840 A | 2/1988 | McVay et al. |
| 4,741,330 A | 5/1988 | Hayhurst |
| 4,741,337 A | 5/1988 | Smith et al. |
| 4,744,363 A | 5/1988 | Hasson |
| 4,745,908 A | 5/1988 | Wardle |
| 4,748,959 A | 6/1988 | Cook et al. |
| 4,750,492 A | 6/1988 | Jacobs |
| 4,753,235 A | 6/1988 | Hasson |
| 4,760,848 A | 8/1988 | Hasson |
| 4,765,335 A | 8/1988 | Schmidt et al. |
| 4,777,949 A | 10/1988 | Perlin |
| 4,779,616 A | 10/1988 | Johnson |
| 4,790,294 A | 12/1988 | Allred et al. |
| 4,796,626 A | 1/1989 | De Vries |
| 4,796,627 A | 1/1989 | Tucker |
| 4,807,626 A | 2/1989 | McGirr |
| 4,819,633 A | 4/1989 | Bauer et al. |
| 4,832,055 A | 5/1989 | Palestrant |
| 4,841,888 A | 6/1989 | Mills et al. |
| 4,869,238 A | 9/1989 | Opie et al. |
| 4,872,579 A | 10/1989 | Palmer |
| 4,873,976 A | 10/1989 | Schreiber |
| 4,890,615 A | 1/1990 | Caspari et al. |
| 4,909,789 A | 3/1990 | Taguchi et al. |
| 4,929,240 A | 5/1990 | Kirsch et al. |
| 4,944,741 A | 7/1990 | Hasson |
| 4,949,927 A | 8/1990 | Madocks et al. |
| 4,955,897 A | 9/1990 | Ship |
| 4,957,498 A | 9/1990 | Caspari et al. |
| 4,977,900 A | 12/1990 | Fehlinge et al. |
| 4,983,176 A | 1/1991 | Cushman et al. |
| 4,988,171 A | 1/1991 | Yokota |

(56) References Cited

U.S. PATENT DOCUMENTS

| | | |
|---|---|---|
| 4,991,567 A | 2/1991 | McCuen, II et al. |
| 4,997,435 A | 3/1991 | Demeter |
| 5,000,683 A | 3/1991 | Brock |
| 5,005,558 A | 4/1991 | Aomori |
| 5,014,407 A | 5/1991 | Boughten et al. |
| 5,015,249 A | 5/1991 | Nakao et al. |
| 5,020,539 A | 6/1991 | Yokoi et al. |
| 5,025,778 A | 6/1991 | Silverstein et al. |
| 5,032,127 A | 7/1991 | Frazee et al. |
| 5,035,231 A | 7/1991 | Kubokawa et al. |
| 5,035,692 A | 7/1991 | Lyon et al. |
| 5,037,433 A | 8/1991 | Wilk et al. |
| 5,041,093 A | 8/1991 | Chu |
| 5,041,129 A | 8/1991 | Hayhurst et al. |
| 5,049,153 A | 9/1991 | Nakao et al. |
| 5,059,201 A | 10/1991 | Asnis |
| 5,068,719 A | 11/1991 | Tsuji |
| 5,088,979 A | 2/1992 | Filipi et al. |
| 5,099,827 A | 3/1992 | Melzer et al. |
| 5,100,418 A | 3/1992 | Yoon et al. |
| 5,100,420 A | 3/1992 | Green et al. |
| 5,108,420 A | 4/1992 | Marks |
| 5,113,846 A | 5/1992 | Hiltebrandt et al. |
| 5,122,136 A | 6/1992 | Guglielmi et al. |
| 5,123,914 A | 6/1992 | Cope |
| 5,133,713 A | 7/1992 | Huang et al. |
| 5,133,735 A | 7/1992 | Slater et al. |
| 5,133,736 A | 7/1992 | Bales, Jr. et al. |
| 5,139,487 A | 8/1992 | Baber |
| 5,141,519 A | 8/1992 | Smith et al. |
| 5,170,775 A | 12/1992 | Tagami |
| 5,171,258 A | 12/1992 | Bales et al. |
| 5,172,225 A | 12/1992 | Takahashi |
| 5,174,276 A | 12/1992 | Crockard |
| 5,176,691 A | 1/1993 | Pierce |
| 5,179,935 A | 1/1993 | Miyagi |
| 5,187,572 A | 2/1993 | Nakamura et al. |
| 5,196,928 A | 3/1993 | Karasawa et al. |
| 5,201,746 A | 4/1993 | Shichman |
| 5,201,752 A | 4/1993 | Brown et al. |
| 5,201,759 A | 4/1993 | Ferzli |
| 5,203,864 A | 4/1993 | Phillips |
| 5,209,747 A | 5/1993 | Knoepfler |
| 5,217,471 A | 6/1993 | Burkhart |
| 5,217,473 A | 6/1993 | Yoon |
| 5,222,508 A | 6/1993 | Contarini |
| 5,222,961 A | 6/1993 | Nakao et al. |
| 5,222,963 A | 6/1993 | Brinkerhoff et al. |
| 5,224,946 A | 7/1993 | Hayhurst et al. |
| 5,234,430 A | 8/1993 | Huebner |
| 5,234,445 A | 8/1993 | Walker et al. |
| 5,238,002 A | 8/1993 | Devlin et al. |
| 5,242,456 A | 9/1993 | Nash et al. |
| 5,250,053 A | 10/1993 | Snyder |
| 5,251,611 A | 10/1993 | Zehel et al. |
| 5,254,126 A | 10/1993 | Filipi et al. |
| 5,261,916 A | 11/1993 | Engelson |
| 5,268,001 A | 12/1993 | Nicholson et al. |
| 5,271,381 A | 12/1993 | Ailinger et al. |
| 5,275,608 A | 1/1994 | Forman et al. |
| 5,282,827 A | 2/1994 | Kensey et al. |
| 5,284,488 A | 2/1994 | Sideris |
| 5,289,817 A | 3/1994 | Williams et al. |
| 5,304,184 A | 4/1994 | Hathaway et al. |
| 5,304,195 A | 4/1994 | Twyford et al. |
| 5,304,203 A | 4/1994 | El-Mallawany |
| 5,304,204 A | 4/1994 | Bregen |
| 5,308,357 A | 5/1994 | Lichtman |
| 5,314,445 A | 5/1994 | Heidmueller nee Degwitz et al. |
| 5,316,543 A | 5/1994 | Eberbach |
| 5,318,528 A | 6/1994 | Heaven et al. |
| 5,325,845 A | 7/1994 | Adair |
| 5,327,914 A | 7/1994 | Shlain |
| 5,330,503 A | 7/1994 | Yoon |
| 5,334,217 A | 8/1994 | Das |
| 5,337,732 A | 8/1994 | Grundfest et al. |
| 5,337,733 A | 8/1994 | Bauerfeind et al. |
| 5,342,376 A | 8/1994 | Ruff |
| 5,345,949 A | 9/1994 | Shlain |
| 5,348,259 A | 9/1994 | Blanco et al. |
| 5,354,298 A | 10/1994 | Lee et al. |
| 5,358,496 A | 10/1994 | Ortiz et al. |
| 5,366,459 A | 11/1994 | Yoon |
| 5,366,479 A | 11/1994 | McGarry et al. |
| 5,372,146 A | 12/1994 | Branch |
| 5,372,604 A | 12/1994 | Trott |
| 5,374,275 A | 12/1994 | Bradley et al. |
| 5,380,334 A | 1/1995 | Torrie et al. |
| 5,382,231 A | 1/1995 | Shlain |
| 5,395,030 A | 3/1995 | Kuramoto et al. |
| 5,395,367 A | 3/1995 | Wilk |
| 5,397,304 A | 3/1995 | Truckai |
| 5,403,326 A | 4/1995 | Harrison et al. |
| 5,403,329 A | 4/1995 | Hinchcliffe |
| 5,417,691 A | 5/1995 | Hayhurst |
| 5,417,699 A | 5/1995 | Klein et al. |
| 5,425,744 A | 6/1995 | Fagan et al. |
| 5,429,598 A | 7/1995 | Waxman et al. |
| 5,431,666 A | 7/1995 | Sauer et al. |
| 5,433,721 A | 7/1995 | Hooven et al. |
| 5,433,727 A | 7/1995 | Sideris |
| 5,437,266 A | 8/1995 | McPherson et al. |
| 5,437,680 A | 8/1995 | Yoon |
| 5,437,681 A | 8/1995 | Meade et al. |
| 5,441,499 A | 8/1995 | Fritzch |
| 5,445,167 A | 8/1995 | Yoon et al. |
| 5,448,989 A | 9/1995 | Heckele |
| 5,458,609 A | 10/1995 | Gordon et al. |
| 5,462,560 A | 10/1995 | Stevens |
| 5,462,561 A | 10/1995 | Voda |
| 5,465,894 A | 11/1995 | Clark et al. |
| 5,470,337 A | 11/1995 | Moss |
| 5,470,338 A | 11/1995 | Whitfield et al. |
| 5,476,470 A | 12/1995 | Fitzgibbons |
| 5,478,354 A | 12/1995 | Tovey et al. |
| 5,480,405 A | 1/1996 | Yoon |
| 5,496,332 A | 3/1996 | Sierra et al. |
| 5,496,334 A | 3/1996 | Klundt et al. |
| 5,499,991 A | 3/1996 | Garman et al. |
| 5,501,691 A | 3/1996 | Goldrath |
| 5,507,811 A | 4/1996 | Koike et al. |
| 5,520,691 A | 5/1996 | Branch |
| 5,520,701 A | 5/1996 | Lerch |
| 5,522,843 A | 6/1996 | Zang |
| 5,527,321 A | 6/1996 | Hinchliffe |
| 5,527,322 A | 6/1996 | Klein et al. |
| 5,527,342 A | 6/1996 | Piertrzak et al. |
| 5,531,759 A | 7/1996 | Kensey et al. |
| 5,531,788 A | 7/1996 | Dibie et al. |
| 5,536,251 A | 7/1996 | Evard et al. |
| 5,540,704 A | 7/1996 | Gordon et al. |
| 5,549,618 A | 8/1996 | Fleenor et al. |
| 5,549,621 A | 8/1996 | Bessler et al. |
| 5,558,665 A | 9/1996 | Kieturakis |
| 5,562,684 A | 10/1996 | Kammerer |
| 5,562,686 A | 10/1996 | Sauer et al. |
| 5,562,688 A | 10/1996 | Riza |
| 5,569,274 A | 10/1996 | Rapacki et al. |
| 5,569,306 A | 10/1996 | Thal |
| 5,571,116 A | 11/1996 | Bolanos et al. |
| 5,571,119 A | 11/1996 | Atala |
| 5,573,496 A | 11/1996 | McPherson et al. |
| 5,573,540 A | 11/1996 | Yoon |
| 5,573,548 A | 11/1996 | Nazre et al. |
| 5,575,801 A | 11/1996 | Habermeyer et al. |
| 5,578,045 A | 11/1996 | Das |
| 5,582,616 A | 12/1996 | Bolduc et al. |
| 5,584,835 A | 12/1996 | Greenfield |
| 5,584,859 A | 12/1996 | Brotz |
| 5,601,557 A | 2/1997 | Hayhurst |
| 5,603,718 A | 2/1997 | Xu |
| 5,613,974 A | 3/1997 | Andreas et al. |
| 5,613,975 A | 3/1997 | Christy |
| 5,624,380 A | 4/1997 | Takayama et al. |

(56) References Cited

U.S. PATENT DOCUMENTS

| | | |
|---|---|---|
| 5,624,381 A | 4/1997 | Kieturakis |
| 5,626,588 A | 5/1997 | Sauer et al. |
| 5,626,614 A | 5/1997 | Hart |
| 5,630,540 A | 5/1997 | Blewett |
| 5,632,752 A | 5/1997 | Buelna |
| 5,643,274 A | 7/1997 | Sander et al. |
| 5,643,295 A | 7/1997 | Yoon |
| 5,643,317 A | 7/1997 | Pavcnik et al. |
| 5,643,320 A | 7/1997 | Lower et al. |
| 5,658,312 A | 8/1997 | Green et al. |
| 5,658,313 A | 8/1997 | Thal |
| 5,662,587 A | 9/1997 | Grundfest et al. |
| 5,662,654 A | 9/1997 | Thompson |
| 5,662,662 A | 9/1997 | Bishop et al. |
| 5,662,663 A | 9/1997 | Shallman |
| 5,665,109 A | 9/1997 | Yoon |
| 5,665,112 A | 9/1997 | Thal |
| 5,667,513 A | 9/1997 | Torrie et al. |
| 5,676,674 A | 10/1997 | Bolanos et al. |
| 5,679,005 A | 10/1997 | Einstein |
| 5,683,417 A | 11/1997 | Cooper |
| 5,683,419 A | 11/1997 | Thal |
| 5,690,655 A | 11/1997 | Hart et al. |
| 5,693,060 A | 12/1997 | Martin |
| 5,700,273 A | 12/1997 | Buelna et al. |
| 5,702,397 A | 12/1997 | Goble et al. |
| 5,702,421 A | 12/1997 | Schneidt |
| 5,704,898 A | 1/1998 | Kokish |
| 5,707,394 A | 1/1998 | Miller et al. |
| 5,709,708 A | 1/1998 | Thal |
| 5,713,903 A | 2/1998 | Sander et al. |
| 5,720,765 A | 2/1998 | Thal |
| 5,724,978 A | 3/1998 | Tenhoff |
| 5,725,552 A | 3/1998 | Kotula et al. |
| 5,728,045 A | 3/1998 | Komi |
| 5,732,707 A | 3/1998 | Widder et al. |
| 5,741,297 A | 4/1998 | Simon |
| 5,741,429 A | 4/1998 | Donadio et al. |
| 5,746,752 A | 5/1998 | Burkhart |
| 5,746,755 A | 5/1998 | Wood et al. |
| 5,749,828 A | 5/1998 | Solomon et al. |
| 5,749,893 A | 5/1998 | Vidal et al. |
| 5,752,963 A | 5/1998 | Allard et al. |
| 5,759,151 A | 6/1998 | Sturges |
| 5,766,169 A | 6/1998 | Fritzsch et al. |
| 5,766,189 A | 6/1998 | Matsuno |
| 5,772,597 A | 6/1998 | Goldberger et al. |
| 5,776,150 A | 7/1998 | Nolan et al. |
| 5,779,719 A | 7/1998 | Klein et al. |
| 5,782,859 A | 7/1998 | Nicholas et al. |
| 5,782,865 A | 7/1998 | Grotz |
| 5,787,897 A | 8/1998 | Kieturakis |
| 5,792,152 A | 8/1998 | Klein et al. |
| 5,792,153 A | 8/1998 | Swain et al. |
| 5,797,929 A | 8/1998 | Andreas et al. |
| 5,797,960 A | 8/1998 | Stevens et al. |
| 5,810,849 A | 9/1998 | Kontos |
| 5,810,851 A | 9/1998 | Yoon |
| 5,810,853 A | 9/1998 | Yoon |
| 5,810,882 A | 9/1998 | Bolduc et al. |
| 5,814,070 A | 9/1998 | Borzone et al. |
| 5,817,107 A | 10/1998 | Schaller |
| 5,817,110 A | 10/1998 | Kronner |
| 5,823,956 A | 10/1998 | Roth et al. |
| 5,824,011 A | 10/1998 | Stone et al. |
| 5,827,298 A | 10/1998 | Hart et al. |
| 5,829,447 A | 11/1998 | Stevens et al. |
| 5,836,955 A | 11/1998 | Buelna et al. |
| 5,840,078 A | 11/1998 | Yerys |
| 5,843,084 A | 12/1998 | Hart et al. |
| 5,843,126 A | 12/1998 | Jameel |
| 5,846,261 A | 12/1998 | Kotula et al. |
| 5,855,614 A | 1/1999 | Stevens et al. |
| 5,860,991 A | 1/1999 | Klein et al. |
| 5,861,003 A | 1/1999 | Latson et al. |
| 5,865,791 A | 2/1999 | Whayne et al. |
| 5,868,760 A | 2/1999 | McGuckin, Jr. |
| 5,868,762 A | 2/1999 | Cragg et al. |
| 5,879,371 A | 3/1999 | Gardiner et al. |
| 5,887,594 A | 3/1999 | Locicero |
| 5,888,247 A | 3/1999 | Benetti |
| 5,891,168 A | 4/1999 | Thal |
| 5,893,856 A | 4/1999 | Jacob et al. |
| 5,895,404 A | 4/1999 | Ruiz |
| 5,897,417 A | 4/1999 | Grey |
| 5,897,562 A | 4/1999 | Bolanos et al. |
| 5,899,920 A | 5/1999 | DeSatnick et al. |
| 5,899,921 A | 5/1999 | Caspari et al. |
| 5,901,895 A | 5/1999 | Heaton et al. |
| 5,902,254 A | 5/1999 | Magram |
| 5,904,647 A | 5/1999 | Ouchi |
| 5,908,381 A | 6/1999 | Aznoian et al. |
| 5,916,147 A | 6/1999 | Boury |
| 5,921,915 A | 7/1999 | Aznoian et al. |
| 5,925,059 A | 7/1999 | Palermo et al. |
| 5,928,260 A | 7/1999 | Chin et al. |
| 5,928,264 A | 7/1999 | Sugarbaker et al. |
| 5,938,586 A | 8/1999 | Wilk et al. |
| 5,941,815 A | 8/1999 | Chang |
| 5,944,738 A | 8/1999 | Amplatz et al. |
| 5,947,983 A | 9/1999 | Solar et al. |
| 5,947,997 A | 9/1999 | Pavcnik et al. |
| 5,948,001 A | 9/1999 | Larsen |
| 5,954,731 A | 9/1999 | Yoon |
| 5,954,732 A | 9/1999 | Hart et al. |
| 5,954,733 A | 9/1999 | Yoon |
| 5,957,937 A | 9/1999 | Yoon |
| 5,961,440 A | 10/1999 | Schweich et al. |
| 5,964,765 A | 10/1999 | Fenton et al. |
| 5,964,782 A | 10/1999 | Lafontaine et al. |
| 5,964,783 A | 10/1999 | Grafton et al. |
| 5,976,127 A | 11/1999 | Lax |
| 5,976,158 A | 11/1999 | Adams et al. |
| 5,976,159 A | 11/1999 | Bolduc et al. |
| 5,980,558 A | 11/1999 | Wiley |
| 5,984,932 A | 11/1999 | Yoon |
| 5,984,933 A | 11/1999 | Yoon |
| 5,993,466 A | 11/1999 | Yoon |
| 5,993,467 A | 11/1999 | Yoon |
| 5,993,476 A | 11/1999 | Groiso |
| 6,013,083 A | 1/2000 | Bennett |
| 6,017,358 A | 1/2000 | Yoon et al. |
| 6,027,523 A | 2/2000 | Schmieding |
| 6,033,430 A | 3/2000 | Bonutti |
| 6,036,699 A | 3/2000 | Andreas et al. |
| 6,042,155 A | 3/2000 | Lockwood |
| 6,045,497 A | 4/2000 | Schweich et al. |
| 6,045,573 A | 4/2000 | Wenstrom et al. |
| 6,050,936 A | 4/2000 | Schweich et al. |
| 6,053,935 A | 4/2000 | Brenneman et al. |
| 6,059,715 A | 5/2000 | Schweich et al. |
| 6,059,719 A | 5/2000 | Yamamoto et al. |
| 6,074,401 A | 6/2000 | Gardiner et al. |
| 6,077,214 A | 6/2000 | Mortier et al. |
| 6,077,281 A | 6/2000 | Das |
| 6,077,291 A | 6/2000 | Das |
| 6,079,414 A | 6/2000 | Roth |
| 6,086,600 A | 7/2000 | Kortenbach |
| 6,086,601 A | 7/2000 | Yoon |
| 6,110,183 A | 8/2000 | Cope |
| 6,113,609 A | 9/2000 | Adams |
| 6,113,611 A | 9/2000 | Allen et al. |
| 6,119,913 A | 9/2000 | Adams et al. |
| 6,149,658 A | 11/2000 | Gardiner et al. |
| 6,152,870 A | 11/2000 | Diener |
| 6,152,935 A | 11/2000 | Kammerer et al. |
| 6,159,146 A | 12/2000 | El Gaverli |
| 6,159,224 A | 12/2000 | Yoon |
| 6,162,168 A | 12/2000 | Schweich et al. |
| 6,165,119 A | 12/2000 | Schweich et al. |
| 6,165,120 A | 12/2000 | Schweich et al. |
| 6,167,889 B1 | 1/2001 | Benetti |
| 6,171,235 B1 | 1/2001 | Konstorum et al. |
| 6,171,320 B1 | 1/2001 | Monassevitch |

(56) References Cited

U.S. PATENT DOCUMENTS

| | | |
|---|---|---|
| 6,174,280 B1 | 1/2001 | Oneda et al. |
| 6,174,323 B1 | 1/2001 | Biggs et al. |
| 6,179,195 B1 | 1/2001 | Adams et al. |
| 6,179,776 B1 | 1/2001 | Adams et al. |
| 6,183,411 B1 | 2/2001 | Mortier et al. |
| 6,197,017 B1 | 3/2001 | Brock et al. |
| 6,197,022 B1 | 3/2001 | Baker |
| 6,214,007 B1 | 4/2001 | Anderson |
| 6,228,023 B1 | 5/2001 | Zaslavsky et al. |
| 6,231,561 B1 | 5/2001 | Frazier et al. |
| 6,234,958 B1 | 5/2001 | Snoke et al. |
| 6,245,079 B1 | 6/2001 | Nobles |
| 6,260,552 B1 | 7/2001 | Mortier et al. |
| 6,261,222 B1 | 7/2001 | Schweich et al. |
| 6,264,602 B1 | 7/2001 | Mortier et al. |
| 6,270,515 B1 | 8/2001 | Linden et al. |
| 6,277,064 B1 | 8/2001 | Yoon |
| 6,283,973 B1 | 9/2001 | Hubbard et al. |
| 6,290,674 B1 | 9/2001 | Roue et al. |
| 6,293,956 B1 | 9/2001 | Crainich et al. |
| 6,296,656 B1 | 10/2001 | Bolduc et al. |
| 6,306,159 B1 | 10/2001 | Schwartz et al. |
| 6,312,437 B1 | 11/2001 | Kortenbach |
| 6,315,715 B1 | 11/2001 | Taylor et al. |
| 6,315,789 B1 | 11/2001 | Cragg |
| 6,322,563 B1 | 11/2001 | Cummings et al. |
| 6,322,580 B1 | 11/2001 | Kanner |
| 6,331,165 B1 | 12/2001 | Turturro et al. |
| 6,332,468 B1 | 12/2001 | Benetti |
| 6,332,863 B1 | 12/2001 | Schweich et al. |
| 6,332,864 B1 | 12/2001 | Schweich et al. |
| 6,332,893 B1 | 12/2001 | Mortier et al. |
| 6,336,940 B1 | 1/2002 | Graf et al. |
| 6,346,074 B1 | 2/2002 | Roth |
| 6,348,064 B1 | 2/2002 | Kanner |
| 6,352,503 B1 | 3/2002 | Matsui et al. |
| 6,355,052 B1 | 3/2002 | Neuss et al. |
| 6,358,197 B1 | 3/2002 | Silverman et al. |
| 6,363,938 B2 | 4/2002 | Saadat et al. |
| 6,368,338 B1 | 4/2002 | Konya et al. |
| 6,368,339 B1 | 4/2002 | Amplatz |
| 6,387,104 B1 | 5/2002 | Pugsley et al. |
| 6,402,679 B1 | 6/2002 | Mortier et al. |
| 6,402,680 B2 | 6/2002 | Mortier et al. |
| 6,406,420 B1 | 6/2002 | McCarthy et al. |
| 6,408,889 B1 | 6/2002 | Komachi |
| 6,423,087 B1 | 7/2002 | Sawada |
| 6,425,859 B1 | 7/2002 | Foley et al. |
| 6,425,911 B1 | 7/2002 | Akerfeldt et al. |
| 6,428,468 B1 | 8/2002 | Knighton et al. |
| 6,432,112 B2 | 8/2002 | Brock et al. |
| 6,440,061 B1 | 8/2002 | Wenner et al. |
| 6,443,944 B1 | 9/2002 | Doshi et al. |
| 6,447,533 B1 | 9/2002 | Adams |
| 6,458,074 B1 | 10/2002 | Matsui et al. |
| 6,468,203 B2 | 10/2002 | Belson |
| 6,478,791 B1 | 11/2002 | Carter et al. |
| 6,485,411 B1 | 11/2002 | Konstorum et al. |
| 6,494,888 B1 | 12/2002 | Laufer et al. |
| 6,506,196 B1 | 1/2003 | Laufer et al. |
| 6,508,828 B1 | 1/2003 | Akerfeldt et al. |
| 6,514,194 B2 | 2/2003 | Schweich et al. |
| 6,527,753 B2 | 3/2003 | Sekine et al. |
| 6,533,796 B1 | 3/2003 | Sauer et al. |
| 6,537,285 B1 | 3/2003 | Hatasaka et al. |
| 6,544,281 B2 | 4/2003 | ELAttrache et al. |
| 6,554,793 B1 | 4/2003 | Pauker et al. |
| 6,554,845 B1 | 4/2003 | Fleenor et al. |
| 6,558,400 B2 | 5/2003 | Deem et al. |
| 6,572,629 B2 | 6/2003 | Kalloo et al. |
| 6,589,160 B2 | 7/2003 | Schweich et al. |
| 6,589,208 B2 | 7/2003 | Ewers et al. |
| 6,592,596 B1 | 7/2003 | Geitz |
| 6,610,007 B2 | 8/2003 | Belson et al. |
| 6,613,059 B2 | 9/2003 | Schaller et al. |
| 6,641,592 B1 | 11/2003 | Sauer et al. |
| 6,656,194 B1 | 12/2003 | Gannoe et al. |
| 6,663,639 B1 | 12/2003 | Laufer et al. |
| 6,689,130 B2 | 2/2004 | Arai et al. |
| 6,695,764 B2 | 2/2004 | Silverman et al. |
| 6,702,826 B2 | 3/2004 | Liddicoat et al. |
| 6,706,048 B2 | 3/2004 | Hermann et al. |
| 6,712,830 B2 | 3/2004 | Esplin |
| 6,716,224 B2 | 4/2004 | Singhatat |
| 6,716,232 B1 | 4/2004 | Vidal et al. |
| 6,719,763 B2 | 4/2004 | Chung et al. |
| 6,719,764 B1 | 4/2004 | Gellman et al. |
| 6,736,828 B1 | 5/2004 | Adams et al. |
| 6,740,098 B2 | 5/2004 | Abrams et al. |
| 6,743,239 B1 | 6/2004 | Kuehn et al. |
| 6,743,240 B2 | 6/2004 | Smith et al. |
| 6,746,460 B2 | 6/2004 | Gannoe et al. |
| 6,746,471 B2 | 6/2004 | Mortier et al. |
| 6,755,843 B2 | 6/2004 | Chung et al. |
| 6,761,685 B2 | 7/2004 | Adams et al. |
| 6,773,440 B2 | 8/2004 | Gannoe et al. |
| 6,773,441 B1 | 8/2004 | Laufer et al. |
| 6,793,621 B2 | 9/2004 | Butler et al. |
| 6,800,056 B2 | 10/2004 | Tartaglia et al. |
| 6,811,532 B2 | 11/2004 | Ogura et al. |
| 6,814,728 B2 | 11/2004 | Ouchi |
| 6,817,974 B2 | 11/2004 | Cooper et al. |
| 6,821,285 B2 | 11/2004 | Laufer et al. |
| 6,835,199 B2 | 12/2004 | McGuckin, Jr. et al. |
| 6,835,200 B2 | 12/2004 | Laufer et al. |
| 6,837,846 B2 | 1/2005 | Jaffe et al. |
| 6,837,849 B2 | 1/2005 | Ogura et al. |
| 6,858,005 B2 | 2/2005 | Ohline et al. |
| 6,869,395 B2 | 3/2005 | Page et al. |
| 6,884,249 B2 | 4/2005 | May et al. |
| 6,890,297 B2 | 5/2005 | Belson |
| 6,899,673 B2 | 5/2005 | Ogura et al. |
| 6,921,361 B2 | 7/2005 | Suzuki et al. |
| 6,932,834 B2 | 8/2005 | Lizardi et al. |
| 6,932,835 B2 | 8/2005 | Bonutti et al. |
| 6,986,781 B2 | 1/2006 | Smith |
| 6,988,987 B2 | 1/2006 | Ishikawa et al. |
| 6,994,715 B2 | 2/2006 | Gannoe et al. |
| 6,997,931 B2 | 2/2006 | Sauer et al. |
| 7,033,370 B2 | 4/2006 | Gordon et al. |
| 7,033,373 B2 | 4/2006 | de la Torre et al. |
| 7,037,324 B2 | 5/2006 | Martinek |
| 7,044,907 B2 | 5/2006 | Belson |
| 7,063,630 B2 | 6/2006 | Cavallaro |
| 7,063,659 B2 | 6/2006 | Goto et al. |
| 7,063,715 B2 | 6/2006 | Onuki et al. |
| 7,083,629 B2 | 8/2006 | Weller et al. |
| 7,083,630 B2 | 8/2006 | DeVries et al. |
| 7,090,684 B2 | 8/2006 | McGuckin et al. |
| 7,125,413 B2 | 10/2006 | Grigoryants et al. |
| 7,153,314 B2 | 12/2006 | Laufer et al. |
| 7,156,863 B2 | 1/2007 | Sonnenschein et al. |
| 7,160,312 B2 | 1/2007 | Saadat |
| 7,163,801 B2 | 1/2007 | Reed |
| 7,211,094 B2 | 5/2007 | Gannoe et al. |
| 7,220,237 B2 | 5/2007 | Gannoe et al. |
| 7,220,266 B2 | 5/2007 | Gambale |
| 7,229,428 B2 | 6/2007 | Gannoe et al. |
| 7,235,086 B2 | 6/2007 | Sauer et al. |
| 7,235,090 B2 | 6/2007 | Buckman et al. |
| 7,261,722 B2 | 8/2007 | McGuckin et al. |
| 7,288,101 B2 | 10/2007 | Deem et al. |
| 7,341,554 B2 | 3/2008 | Sekine et al. |
| 7,344,545 B2 | 3/2008 | Takemoto et al. |
| 7,347,863 B2 | 3/2008 | Rothe et al. |
| 7,361,180 B2 | 4/2008 | Saadat et al. |
| 7,371,244 B2 | 5/2008 | Chatlynne et al. |
| 7,390,329 B2 | 6/2008 | Westra et al. |
| 7,399,304 B2 | 7/2008 | Gambale et al. |
| 7,416,554 B2 | 8/2008 | Lam et al. |
| 7,503,922 B2 | 3/2009 | Deem et al. |
| 7,510,559 B2 | 3/2009 | Deem et al. |
| 7,520,884 B2 | 4/2009 | Swanstrom et al. |
| 7,527,590 B2 | 5/2009 | Suzuki et al. |

(56) References Cited

U.S. PATENT DOCUMENTS

| | | |
|---|---|---|
| 7,534,248 B2 | 5/2009 | Mikkaichi et al. |
| 7,549,983 B2 | 6/2009 | Roue et al. |
| 7,571,729 B2 | 8/2009 | Saadat et al. |
| 7,601,159 B2 | 10/2009 | Ewers et al. |
| 7,618,425 B2 | 11/2009 | Yamamoto et al. |
| 7,618,426 B2 | 11/2009 | Ewers et al. |
| 7,621,925 B2 | 11/2009 | Saadat et al. |
| 7,678,135 B2 | 3/2010 | Maahs et al. |
| 7,686,819 B2 | 3/2010 | Kortenbach |
| 7,695,493 B2 | 4/2010 | Saadat et al. |
| 7,703,459 B2 | 4/2010 | Saadat et al. |
| 7,704,264 B2 | 4/2010 | Ewers et al. |
| 7,713,277 B2 | 5/2010 | Laufer et al. |
| 7,722,633 B2 | 5/2010 | Laufer et al. |
| 7,727,246 B2 | 6/2010 | Sixto et al. |
| 7,731,757 B2 | 6/2010 | Taylor et al. |
| 7,736,372 B2 | 6/2010 | Reydel et al. |
| 7,736,373 B2 | 6/2010 | Laufer et al. |
| 7,736,374 B2 | 6/2010 | Vaughan et al. |
| 7,736,378 B2 | 6/2010 | Maahs et al. |
| 7,736,379 B2 | 6/2010 | Ewers et al. |
| 7,744,613 B2 | 6/2010 | Ewers et al. |
| 7,785,252 B2 | 8/2010 | Danitz |
| 7,846,180 B2 | 12/2010 | Cerier |
| 7,857,823 B2 | 12/2010 | Laufer et al. |
| 7,871,419 B2 | 1/2011 | Devellian |
| 7,896,893 B2 | 3/2011 | Laufer et al. |
| 7,918,845 B2 | 4/2011 | Saadat et al. |
| 7,918,869 B2 | 4/2011 | Saadat et al. |
| 7,931,661 B2 | 4/2011 | Saadat et al. |
| 7,942,884 B2 | 5/2011 | Vahid et al. |
| 7,942,898 B2 | 5/2011 | Ewers et al. |
| 7,951,165 B2 | 5/2011 | Golden et al. |
| 7,955,340 B2 | 6/2011 | Michlitsch et al. |
| 7,993,368 B2 | 8/2011 | Gambale et al. |
| 8,057,511 B2 | 11/2011 | Flores et al. |
| 8,066,719 B2 | 11/2011 | Ewers et al. |
| 8,087,413 B2 | 1/2012 | Saadat et al. |
| 8,142,448 B2 | 3/2012 | Pasricha et al. |
| 8,157,817 B2 | 4/2012 | Bonadio et al. |
| 8,157,836 B2 | 4/2012 | Adams |
| 8,187,323 B2 | 5/2012 | Mortier et al. |
| 8,206,417 B2 | 6/2012 | Maahs et al. |
| 8,216,252 B2 | 7/2012 | Vaughan et al. |
| 8,257,389 B2 | 9/2012 | Chanduszko et al. |
| 8,257,394 B2 | 9/2012 | Saadat et al. |
| 8,277,373 B2 | 10/2012 | Maahs et al. |
| 8,298,291 B2 | 10/2012 | Ewers et al. |
| 8,308,765 B2 | 11/2012 | Saadat et al. |
| 8,444,657 B2 | 5/2013 | Saadat et al. |
| 8,512,229 B2 | 8/2013 | Saadat et al. |
| 8,517,923 B2 | 8/2013 | Belson |
| 8,562,516 B2 | 10/2013 | Saadat et al. |
| 8,562,646 B2 | 10/2013 | Gellman et al. |
| 8,574,243 B2 | 11/2013 | Saadat et al. |
| 8,613,749 B2 | 12/2013 | Deem et al. |
| 8,628,541 B2 | 1/2014 | Saadat et al. |
| 8,795,274 B2 | 8/2014 | Hanna |
| 2002/0019649 A1 | 2/2002 | Sikora et al. |
| 2002/0068945 A1 | 6/2002 | Sixto et al. |
| 2002/0077524 A1 | 6/2002 | Schweich et al. |
| 2002/0082621 A1 | 6/2002 | Schurr et al. |
| 2002/0082622 A1 | 6/2002 | Kane |
| 2002/0087048 A1 | 7/2002 | Brock et al. |
| 2003/0225312 A1 | 12/2003 | Suzuki et al. |
| 2003/0236505 A1 | 12/2003 | Bonadio et al. |
| 2004/0059346 A1 | 3/2004 | Adams et al. |
| 2004/0122456 A1 | 6/2004 | Saadat et al. |
| 2004/0176784 A1 | 9/2004 | Okada |
| 2004/0193008 A1 | 9/2004 | Jaffe et al. |
| 2004/0193009 A1 | 9/2004 | Jaffe et al. |
| 2004/0193117 A1 | 9/2004 | Laufer et al. |
| 2004/0199052 A1 | 10/2004 | Banik et al. |
| 2004/0215216 A1 | 10/2004 | Gannoe et al. |
| 2004/0249362 A1 | 12/2004 | Levine et al. |
| 2004/0249367 A1 | 12/2004 | Saadat et al. |
| 2004/0249395 A1 | 12/2004 | Mikkaichi et al. |
| 2005/0004576 A1 | 1/2005 | Benderev |
| 2005/0065401 A1 | 3/2005 | Saadat et al. |
| 2005/0075653 A1 | 4/2005 | Saadat et al. |
| 2005/0113640 A1 | 5/2005 | Saadat et al. |
| 2005/0192629 A1 | 9/2005 | Saadat et al. |
| 2005/0203488 A1 | 9/2005 | Michlitsch et al. |
| 2005/0250984 A1 | 11/2005 | Lam et al. |
| 2005/0250985 A1 | 11/2005 | Saadat et al. |
| 2005/0250986 A1 | 11/2005 | Rothe et al. |
| 2005/0250987 A1 | 11/2005 | Ewers et al. |
| 2005/0250988 A1 | 11/2005 | Ewers et al. |
| 2005/0251091 A1 | 11/2005 | Saadat et al. |
| 2005/0251159 A1 | 11/2005 | Ewers et al. |
| 2005/0251176 A1 | 11/2005 | Swanstrom et al. |
| 2005/0251189 A1 | 11/2005 | Saadat et al. |
| 2005/0251205 A1 | 11/2005 | Ewers et al. |
| 2005/0267335 A1 | 12/2005 | Okada et al. |
| 2005/0272977 A1 | 12/2005 | Saadat et al. |
| 2005/0277975 A1 | 12/2005 | Saadat et al. |
| 2006/0009789 A1 | 1/2006 | Gambale et al. |
| 2006/0020274 A1 | 1/2006 | Ewers et al. |
| 2006/0020276 A1 | 1/2006 | Saadat et al. |
| 2006/0100579 A1 | 5/2006 | Maahs et al. |
| 2006/0135971 A1 | 6/2006 | Swanstrom et al. |
| 2006/0161185 A1 | 7/2006 | Saadat et al. |
| 2006/0178560 A1 | 8/2006 | Saadat et al. |
| 2006/0178562 A1 | 8/2006 | Saadat et al. |
| 2006/0183975 A1 | 8/2006 | Saadat et al. |
| 2006/0184161 A1 | 8/2006 | Maahs et al. |
| 2006/0237022 A1 | 10/2006 | Chen et al. |
| 2006/0237023 A1 | 10/2006 | Cox et al. |
| 2006/0247495 A1 | 11/2006 | Bacher et al. |
| 2006/0258909 A1 | 11/2006 | Saadat et al. |
| 2006/0271073 A1 | 11/2006 | Lam et al. |
| 2007/0123840 A1 | 5/2007 | Cox |
| 2007/0142849 A1 | 6/2007 | Ewers et al. |
| 2007/0282358 A1 | 12/2007 | Remiszewski et al. |
| 2009/0030446 A1 | 1/2009 | Measamer |
| 2010/0057084 A1 | 3/2010 | Hanna |
| 2011/0082347 A1 | 4/2011 | Okoniewski |
| 2012/0271329 A1* | 10/2012 | Nakamura ........... A61B 17/062 606/147 |

OTHER PUBLICATIONS

Taiwan Intellectual Property Office (TIPO), Search Report Dated Apr. 11, 2016 for Taiwan Patent Application No. 102113739, 1 pages.

* cited by examiner

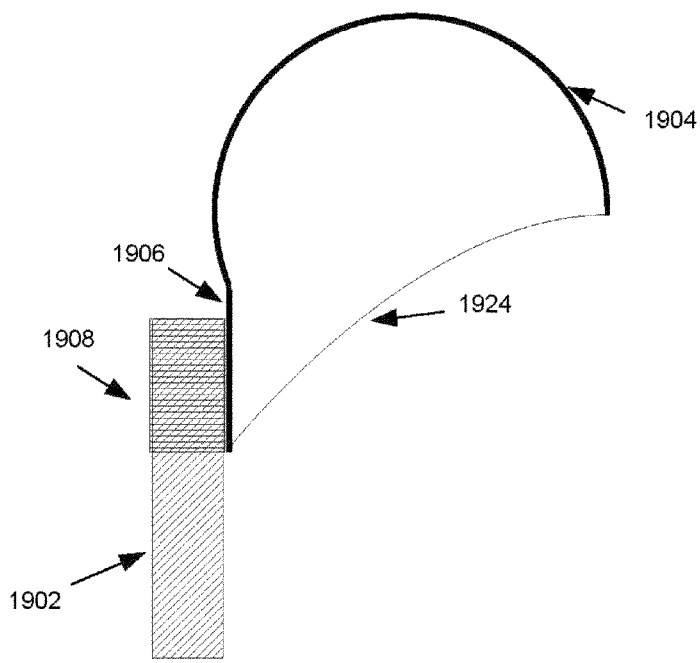
FIG. 19A
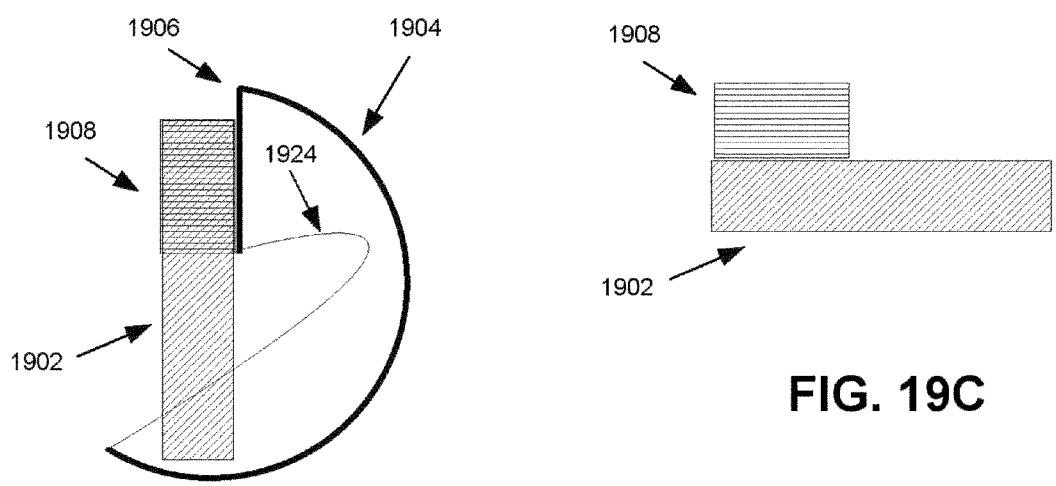
FIG. 19B
FIG. 19C

MANIPULATOR FOR GRASPING TISSUE

CLAIM OF PRIORITY

This application is a continuation of U.S. patent application Ser. No. 13/449,190 (now U.S. Pat. No. 9,265,514), filed Apr. 17, 2012 entitled "MANIPULATOR FOR GRASPING TISSUE" which application is incorporated herein by reference in its entirety.

FIELD OF THE INVENTION

This invention relates generally to manipulators used for grasping and holding objects and tissue.

BACKGROUND OF THE INVENTION

Several methods are known for surgically grasping tissue using manipulators. Stability of grasping is commonly increased by roughening and toothing in several patterns to thereby increase the adhesion of contact surfaces of the manipulator. Depth of grasping is commonly increased by taking on a thread, using multiple manipulators applied in several steps, or stitching with a curved needle and tying to seal veins lying in deeper layers.

As technology has developed, there has been an increase in the need for manipulators which are capable of being used in tighter spaces and which are capable of being used in more difficult medical procedures. The application of manipulators in narrow spaces, such as in body cavities or through body orifices, is usually complicated and often requires the use of multiple manipulators applied in several steps, which increases the duration and complexity of a medical procedure, and thus the likelihood of complications.

There is a need to develop a manipulator that reduces the imperfections of known solutions, which is preferably easy and quick to apply, which is suitable for pulling in and grasping tissues with large surface and mass, and which is suitable for manipulation in deeper layers.

SUMMARY

In accordance with an embodiment of the invention, a manipulator adapted to grasp tissue comprises a first arm, a first grasping surface connected to and extending from the first arm, a second arm, and a second grasping surface connected to and extending from the second arm. The first arm and the second arm are separated by a distance. The first grasping surface and the second grasping surface extend toward each other, and are each arranged at an initial position relative to the respective arm from which they extend by a spring force. When the first arm and second arm are actuated to reduce the distance between them, the first grasping surface and the second grasping surface are contactable such that the first grasping surface and the second grasping surface resist actuation of the first arm and the second arm. The first arm and second arm can be further actuated such that a counter force is applied to the first grasping surface and the second grasping surface. When the counter force overcomes the spring force of the first grasping surface and the second grasping surface, the first grasping surface and the second grasping surface pivot at respective pivot points so that the distance between the distal ends of the first and second arms is reduced.

In some embodiments of the invention, the spring force is applied to the first and second grasping surfaces by one of a leaf spring, a torsion spring, a hydraulic device, a pneumatic device, and a magnetic device. In some embodiments of the invention, the first and second grasping surfaces are leaf springs having a parabolic shape and the first and second pivot points are fixed points at which the first and second grasping surfaces are bendable. In some embodiments of the invention, the first and second grasping surfaces are circular in cross-section and are connected to the respective pivot points off-center.

In some embodiments of the invention, the first arm and the second arm are hingedly connected at respective proximal ends, and can optionally be manually actuatable by a user. In other embodiments, the first arm and the second arm are remotely actuatable.

In some embodiments of the invention, the manipulator further comprises a first rigid grasper connected with the first arm and a second rigid grasper connected with the second arm. When the first grasping surface and the second grasping surface reach a maximum actuation, the tissue drawn toward the manipulator is firmly held between the first rigid grasper and the second rigid grasper.

In some embodiments of the invention, the manipulator further comprises a therapeutic or diagnostic device having a first portion connected with the first arm and a second portion connected with the second arm. When the first grasping surface and the second grasping surface reach a threshold, the therapeutic or diagnostic device can be operated. In some embodiments, the therapeutic or diagnostic device is a vein sealer. When the first grasping surface and the second grasping surface reach a threshold actuation, the first vein sealer portion and the second vein sealer portion can be operated to seal a vein held therebetween. In some embodiments of the invention, the first and second vein sealer portions are a bipolar electrode pair. In some embodiments of the invention, the first and second vein sealer portions are a clip applying pair of forceps.

BRIEF DESCRIPTION OF THE DRAWINGS

FIGS. 19A and 19B are partial top views of an alternative embodiment of a manipulator in accordance with the present invention in an open and closed configuration, respectively.

FIG. 19C is a partial side view of the manipulator of FIGS. 19A and 19B.

FIGS. 29A-29C illustrate an embodiment of an advanceable endoscope in accordance with the present invention.

DETAILED DESCRIPTION

Figure 1A:
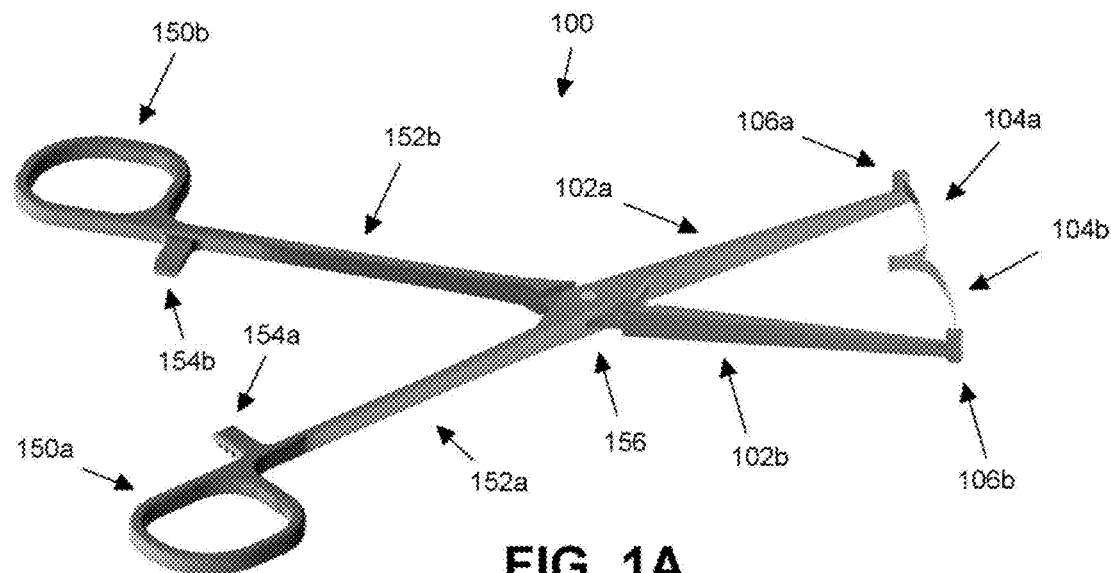
FIG. 1A is a perspective view of an embodiment of a manipulator in accordance with the present invention including grasping surfaces for drawing tissue toward the manipulator.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

FIGS. 1A-1I illustrate an embodiment of a manipulator 100 in accordance with the present invention adapted for grasping and pulling tissues. The manipulator 100 comprises a pair of arms 102a, 102b each of which is connected with a grasping surface 104a, 104b at a pivot point 106a, 106b. The grasping surfaces 104a, 104b are leaf springs that resemble fingers having a semi-parabolic shape that curve outward with a convex orientation relative to respective arms 102a, 102b. The pivot points 106a, 106b are fixed points at which the grasping surfaces 104a, 104b are fixed and about which the grasping surfaces 104a, 104b bend. As shown, the arms 102a, 102b of the manipulator 100 resemble a pair of forceps. Levers 152a, 152b connected at a hinge 156 actuate the arms 102a, 102b when urged together. Proximal ends of the levers 152a, 152b includes finger loops 150a, 150b, and a locking mechanism 154a, 154b to allow the manipulator 100 to act as a clamp to fix tissue in place. The manipulator can be useful, for example, in combination with endoscopes, enabling a large quantity of tissue on a large surface to be precisely grasped. All of the embodiments of manipulators described herein can be hand actuated, for example as a pair of forceps, or alternatively arms of a manipulator can extend from a non-hand actuated tool such as a robotic device controlled by a physician or controlled by an automated system.

Figure 1B:
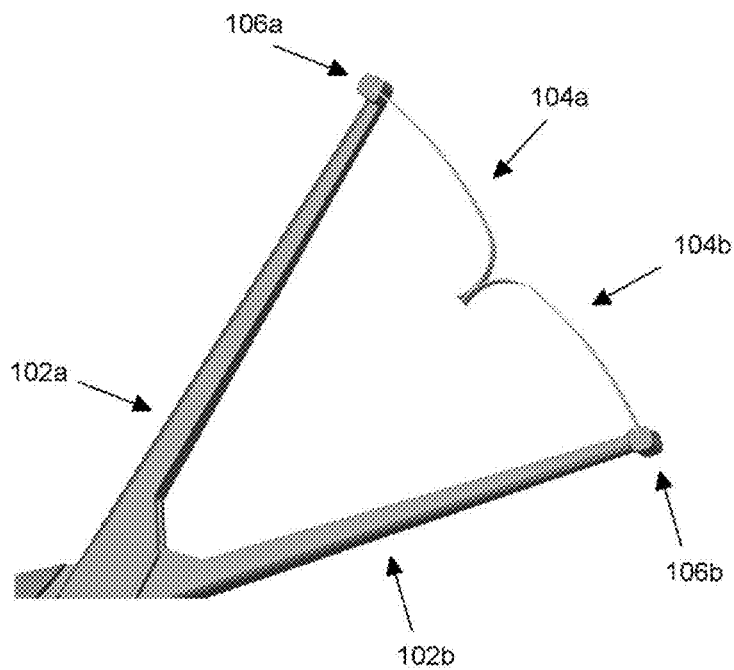
FIG. 1B is a detail view of the grasping surfaces of the manipulator of FIG. 1A.
Figures 1C, 1D:
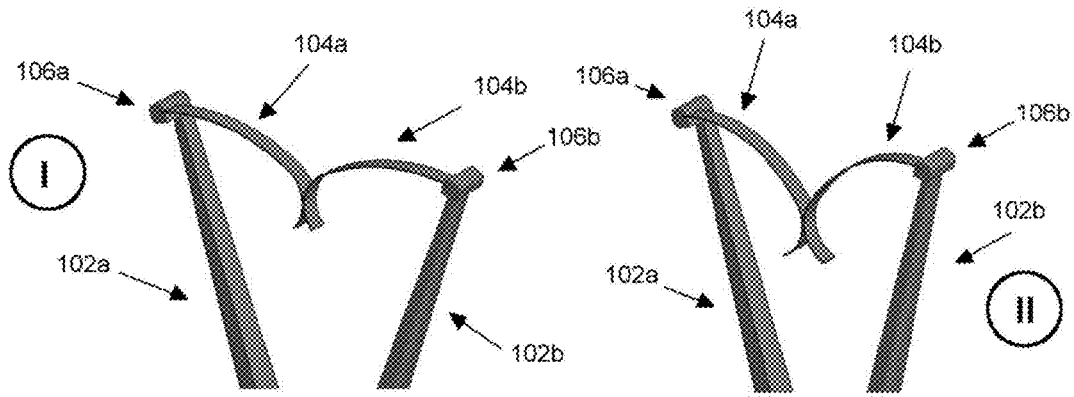
FIGS. 1C-1H are a sequence of detailed views of the grasping surfaces of the manipulator of FIGS. 1A and 1B being actuated and released.
Figures 1E, 1F:
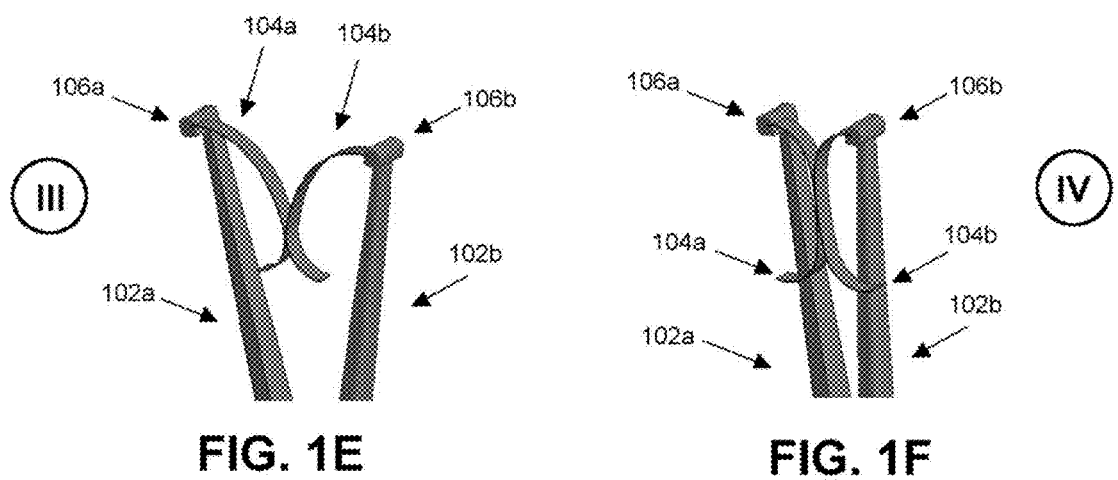
Figures 1G, 1H:
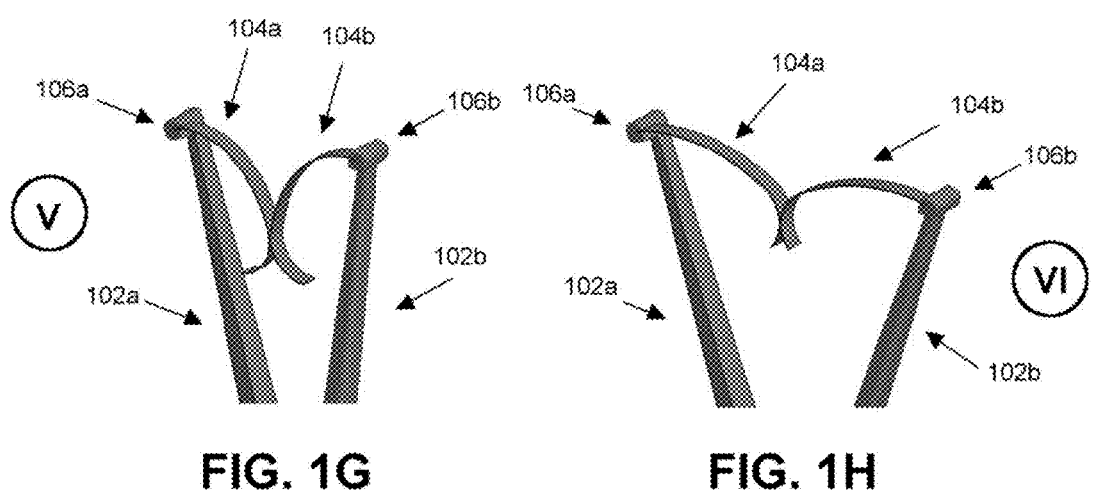

In FIGS. 1A and 1B, the manipulator 100 is open, in that the grasping surfaces 104a, 104b are arranged to contact tissue for grasping. Once the grasping surfaces 104a, 104b are contacted to the target tissue, the manipulator 100 can be actuated to draw tissue into the manipulator 100 (i.e., toward the user holding the manipulator). The spring force of the grasping surfaces 104a, 104b and optional roughing and/or toothing of the grasping surfaces 104a, 104b resist slippage of the tissue held therebetween. Referring to FIGS. 1C-1H, the arrangement of the grasping surfaces 104a, 104b relative to each other is shown at stages I-IV of actuation of the manipulator 100 and at stages V-VI of release of the manipulator 100. As can be seen, the grasping surfaces 104a, 104b are offset from the arms 102a, 102b of the manipulator by the pivot points 106a, 106b which extend laterally away from the arms 102a, 102b. That is, the grasping surfaces 104a, 104b are offset from a plane defined by the arms 102a, 102b. This offset allows the grasping surfaces 104a, 104b to avoid physical interference with the arms 102a, 102b as the arms 102a, 102b are actuated toward each other. This can be seen most clearly in FIG. 1F, where the distal ends of the grasping surfaces 104a, 104b overlap the arms 102a, 102b. As can be seen, the grasping surfaces 104a, 104b contact each other, and the grasping surfaces 104a, 104b urge each other away from the distal ends of the arms 102a, 102b (i.e., the pivot points 106a, 106b) toward the proximal ends of the arms 102a, 102b. Where tissue is arranged between the contact points, the tissue is drawn into the manipulator 100. This can be seen, for example, in FIGS. 14A and 14B described below. As shown in FIG. 1F, as actuation proceeds, the grasping surfaces 104a, 104b bend at the pivot points 106a, 106b until relatively flat portions of the grasping surfaces 104a, 104b contact each other. Where tissue is arranged between the grasping surfaces 104a, 104b, the relatively flat portions provide increased surface area, including any roughened and/or toothed surface area, for securing the tissue and preventing slippage when the locking mechanism 154a, 154b of the manipulator 100 is engaged to fix the tissue in place. As can be seen in FIGS. 1G and 1H, as the manipulator 100 is released, the spring force of the grasping surfaces 104a, 104b urge the grasping surfaces 104a, 104b (and consequently the arms 102a, 102b) apart to their original position.

Figure 1I:
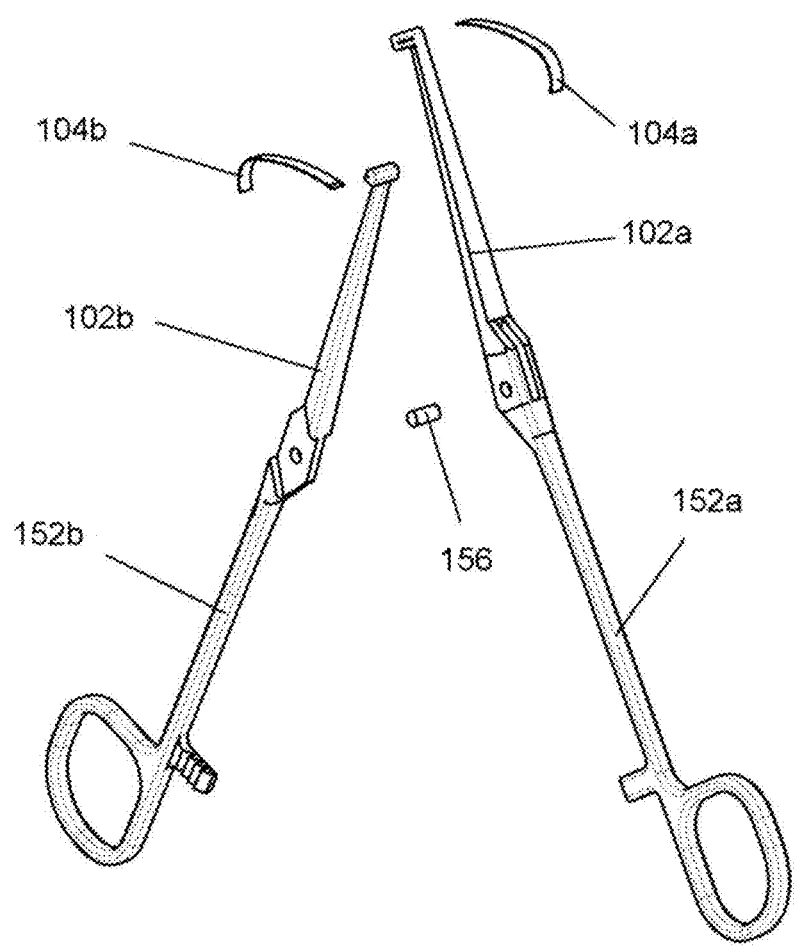
FIG. 1I is an exploded view of the manipulator of FIGS. 1A-1H.

FIG. 1I is an exploded view of the manipulator 100 of FIGS. 1A-1H. In some embodiments, manipulators in accordance with the present invention can be made from a sterilizable, durable material, such as surgical grade stainless steel or polyether ether ketone (PEEK). In other embodiments, for example where a disposable instrument is desired for use, manipulators in accordance with the present invention can be made of a thermopolymer or combination of polymers. In other embodiments, manipulators in accordance with the present invention can be made of a combination of materials. For example, manipulators in accordance with the present invention can comprise levers and arms made from a metal, such as surgical grade stainless steel connected with a head including the grasping surfaces made of a polymer. One of ordinary skill in the art, upon reflecting on the teachings herein and the materials used in surgical and medical procedures, will appreciate the myriad different materials with which manipulators in accordance with the present invention can be formed.

Figure 2A:
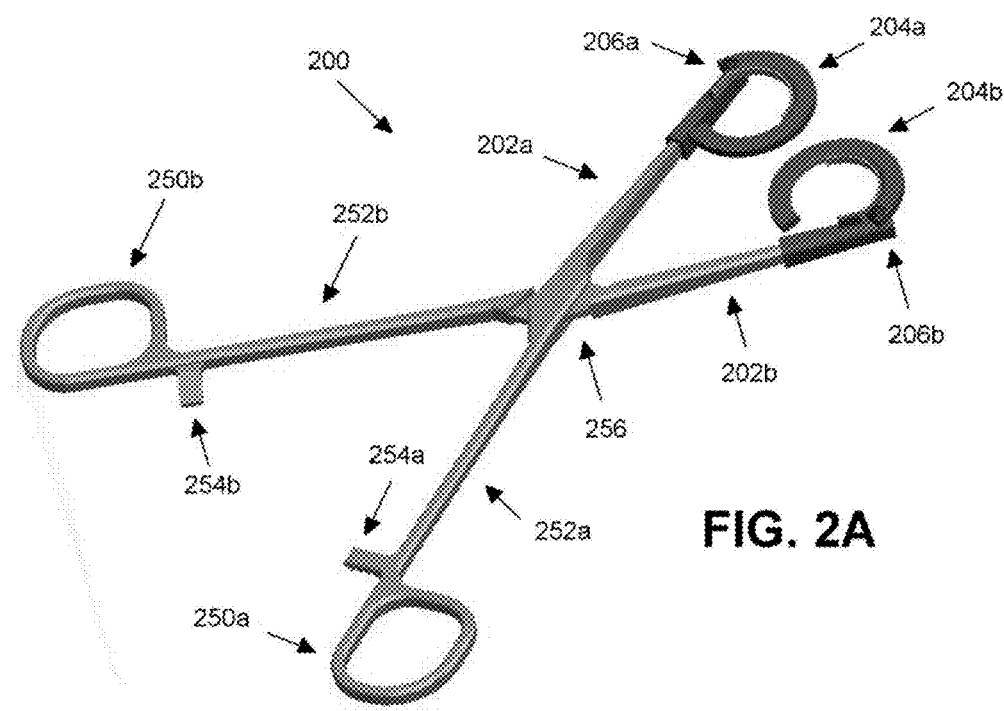
FIG. 2A is a perspective view of an alternative embodiment of a manipulator in accordance with the present invention comprising disposable heads each including a distal portion of an arm and a grasping surface.
Figure 2B:
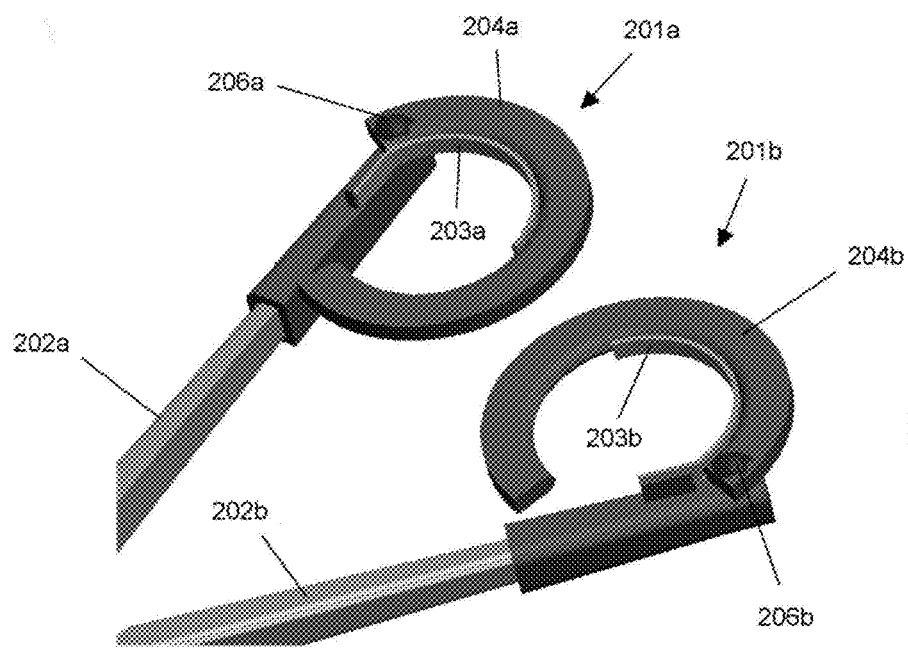
FIG. 2B is a detail view of the grasping surfaces of the manipulator of FIG. 2A.

FIGS. 2A and 2B illustrate an alternative embodiment of a manipulator 200 in accordance with the present invention adapted for grasping and pulling tissues. The manipulator 200 comprises a pair of arms 202a, 202b each of which is connected with a removable head 201a, 201b. The removable head 201a, 201b includes a grasping surface 204a, 204b connected with the head 201a, 201b at a pivot point 206a, 206b. The grasping surfaces 204a, 204b are rigid or semi-rigid surfaces extending about one-half to three-quarters of the circumference of a ring and connected with a pivot point 206a, 206b near one end, although in other embodiments the grasping surfaces can have a different shape. A leaf spring 203a, 203b is nested within the inner surface of each of the grasping surfaces 204a, 204b applying a bias spring force to resist the grasping surfaces 204a, 204b pivoting toward each other. The pivot points 206a, 206b include shafts that allow the grasping surfaces 204a, 204b to pivot relative to the head 201a, 201b (as opposed to merely allowing bending as in the previous embodiment). As above, the manipulator 200 further comprises levers 252a, 252b connected at a hinge 256 actuate the arms 202a, 202b when urged together. Proximal ends of the levers 252a, 252b includes finger loops 250a, 250b, and a locking mechanism 254a, 254b to allow the manipulator 200 to act as a clamp to fix tissue in place.

Once the grasping surfaces 204a, 204b are contacted to the target tissue, the manipulator 200 can be actuated to draw tissue into the manipulator 200 (i.e., toward the user holding the manipulator). As can be seen in FIG. 2B, the grasping surfaces 204a, 204b are offset from the arms 202a, 202b of the manipulator 200. That is, the grasping surfaces 204a, 204b are offset from a plane defined by the arms 202a, 202b to allow the grasping surfaces 204a, 204b to avoid physical interference with the arms 202a, 202b as the arms 202a, 202b are actuated toward each other. As the arms 202a, 202b are actuated, the grasping surfaces 204a, 204b approach each other and captured tissue arranged therebetween urge the grasping surfaces 204a, 204b to rotate inwardly so that the hinge points 206a, 206b can come together. The tissue arranged between the grasping surfaces 204a, 204b is drawn into the manipulator 200. When the manipulator 200 is released, the spring force of the leaf springs 203a, 203b urge the grasping surfaces 204a, 204b to rotate in opposite directions, pushing the arms 202a, 202b apart to their original position.

Figure 3:
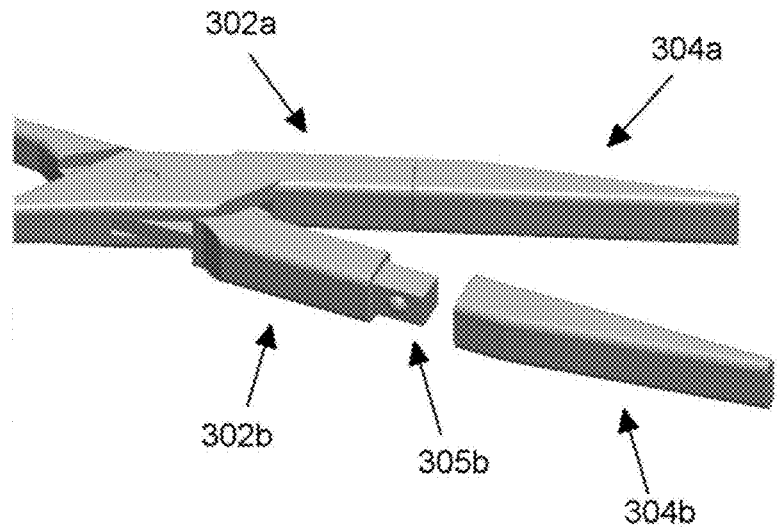
FIGS. 3 and 4 are partial perspective views of attachment mechanisms for attaching grasping surfaces to manipulator arms.
Figure 4:
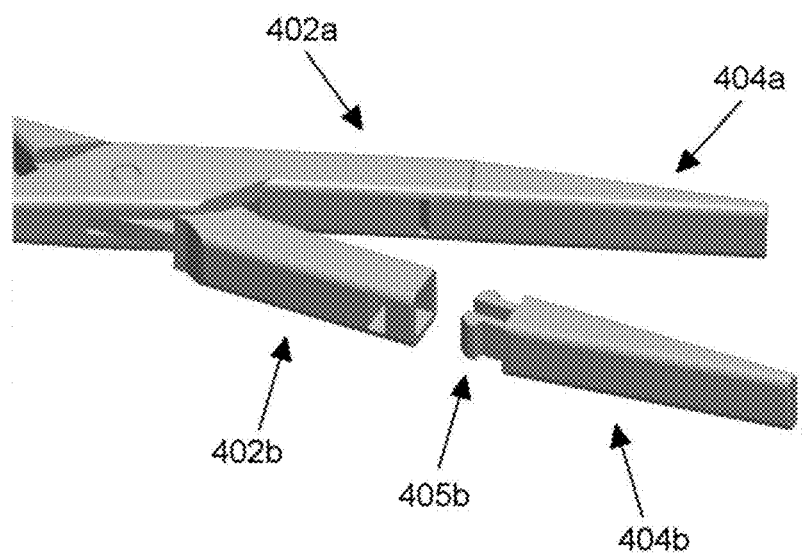

As mentioned, the embodiment of FIGS. 2A and 2B include detachable heads 201a, 201b. Use of a detachable heads can allow the manipulator 200 to be fit with appropriately sized heads based on the procedure performed, with heads including additional therapeutic and/or diagnostic tools such as vein sealers. Use of detachable heads can also allow recently used heads to be replaced with recently sterilized heads. The detachable heads can be made from metal, such as surgical grade stainless steel, or the detachable heads can be formed of a thermopolymer for reduced cost and disposability, for example. The manipulator can also be semi-disposable, with a levers and arms being made from surgical grade stainless steel and detachable heads being made of a thermopolymer, for example. FIGS. 3 and 4 illustrate two different mechanisms for connecting a detachable head with the arms of a manipulator. FIG. 3 includes a spring biased sphere 305b extending from an attachment point of an arm 302b that pops into a complementary feature (not shown) in the inner surface of the head 304b. FIG. 4 includes a pair of tines 405b extending from the head 404b that are inserted into a hollow cavity of the arm 402b until the head 404b and tines 405b latch into complementary features of the arm 402b.

Figure 5A:
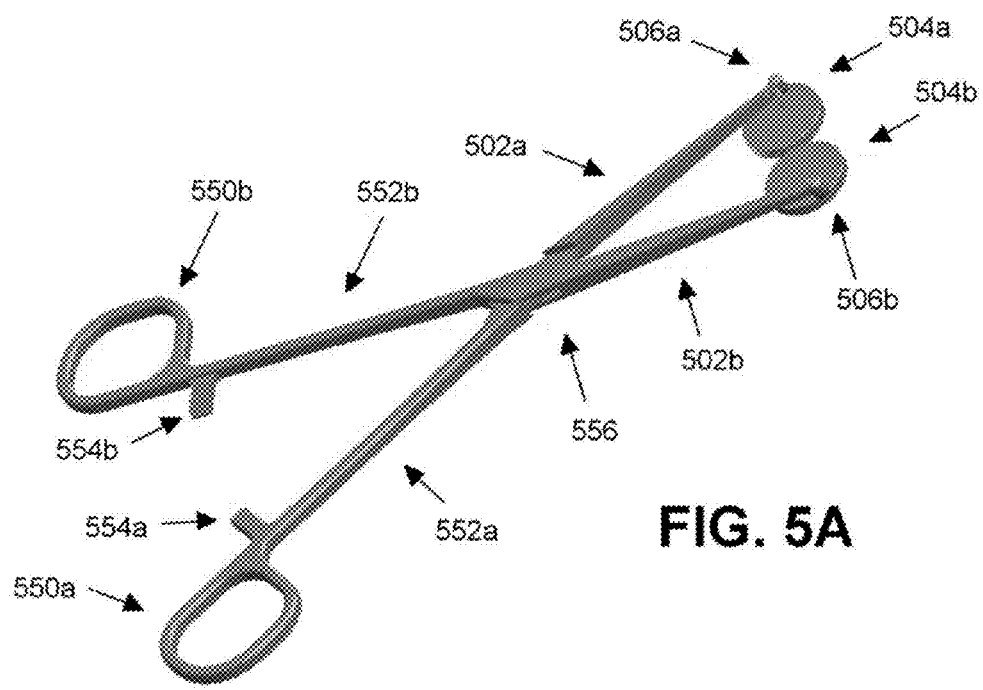
FIG. 5A is a perspective view of an alternative embodiment of a manipulator in accordance with the present invention.
Figure 5B:
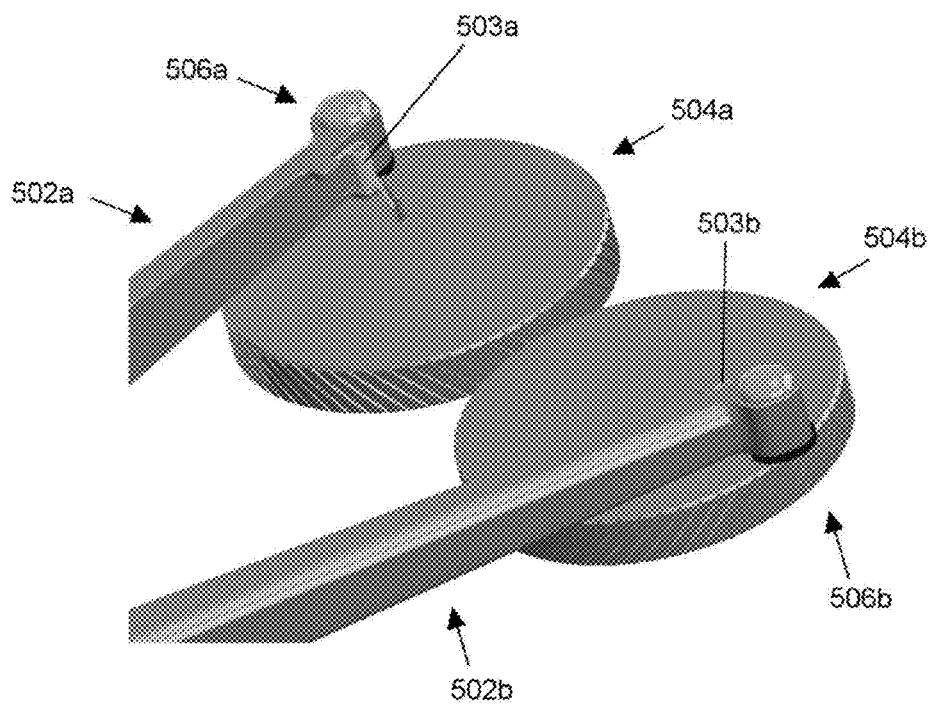
FIG. 5B is a detail view of grasping surfaces of the manipulator of FIG. 5A.

FIGS. 5A and 5B illustrate an alternative embodiment of a manipulator 500 in accordance with the present invention adapted for grasping and pulling tissues. The manipulator 500 comprises a pair of arms 502a, 502b each of which is connected with a grasping surface 504a, 504b at a pivot point 506a, 506b. The grasping surfaces 504a, 504b are rigid or semi-rigid surfaces which are cylindrically shaped and connected to the pivot points 506a, 506b off-center, near an edge of the grasping surfaces 504a, 504b. In other embodiments, the grasping surfaces need not be circular in cross-section. For example, the grasping surfaces can be elliptical in cross-section. Helical torsion springs 503a, 503b are arranged between respective arms 502a, 502b and grasping surfaces 504a, 504b to apply a bias spring force to resist the grasping surfaces 504a, 504b pivoting toward each other.

The pivot points 506a, 506b include shafts that allow the grasping surfaces 504a, 504b to pivot relative to the arms 502a, 502b. As above, the manipulator 500 further comprises levers 552a, 552b connected at a hinge 556 actuate the arms 502a, 502b when urged together. Proximal ends of the levers 552a, 552b includes finger loops 550a, 550b, and a locking mechanism 554a, 554b to allow the manipulator 500 to act as a clamp to fix tissue in place.

Once the grasping surfaces 504a, 504b are contacted to the target tissue, the manipulator 500 can be actuated to draw tissue into the manipulator 500 (i.e., toward the user holding the manipulator). As can be seen in FIG. 5B, the grasping surfaces 504a, 504b are offset from the arms 502a, 502b of the manipulator 500. That is, the grasping surfaces 504a, 504b are offset from a plane defined by the arms 502a, 502b to allow the grasping surfaces 504a, 504b to avoid physical interference with the arms 502a, 502b as the arms 502a, 502b are actuated toward each other. As the arms 502a, 502b are actuated, the grasping surfaces 504a, 504b approach each other and captured tissue arranged therebetween urge the grasping surfaces 204a, 204b to rotate inwardly so that the hinge points 506a, 506b can come together. The tissue arranged between the grasping surfaces 504a, 504b is drawn into the manipulator 500. The grasping surfaces 504a, 504b are textured along their edges to resist slippage of tissue held therebetween. The texture shown includes a series of diagonal grooves. However, myriad different texture patterns and features such as roughening, toothing, and grooving can be used with any of the embodiments of manipulators described herein, some patterns of which are described below. When the manipulator 500 is released, the spring force of the helical torsion springs 503a, 503b urge the grasping surfaces 504a, 504b to rotate in opposite directions, pushing the arms 502a, 502b apart to their original position.

Figure 6:
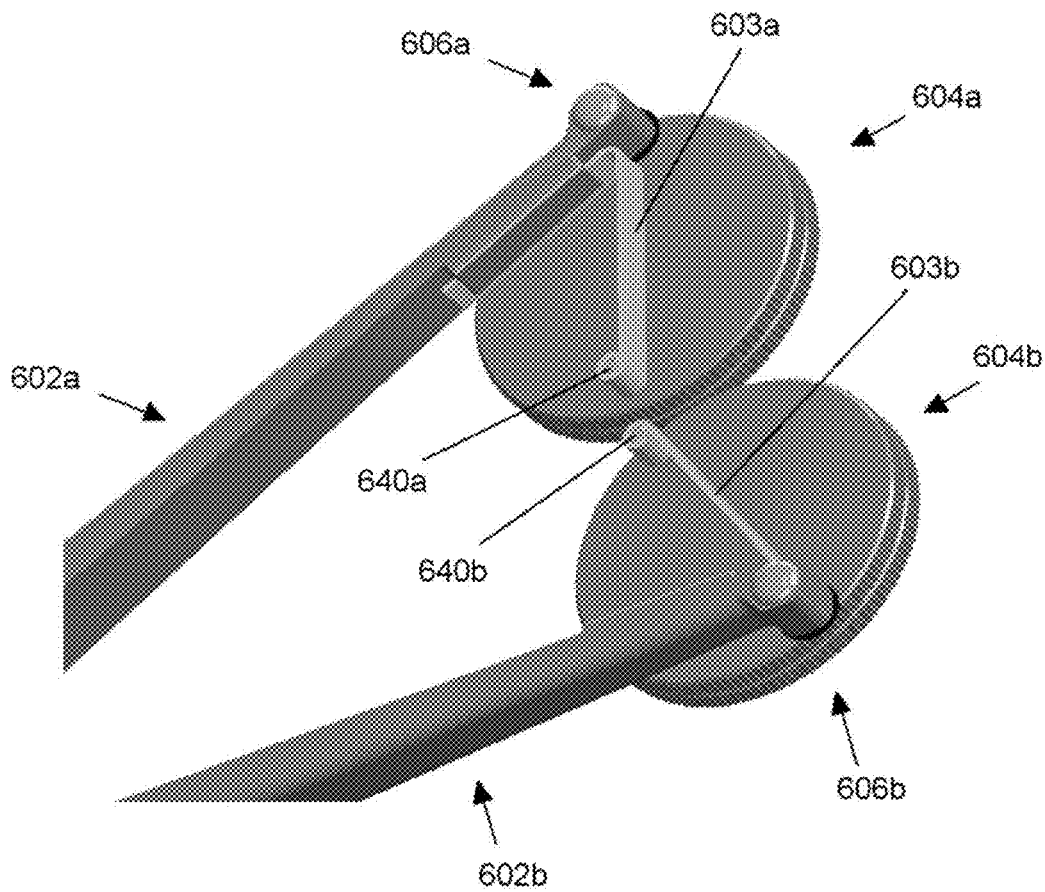
FIG. 6 is a detail view of grasping surfaces of an alternative manipulator.

FIG. 6 illustrates an alternative embodiment of a manipulator 600 in accordance with the present invention adapted for grasping and pulling tissues. The manipulator 600 resembles the manipulator 500 of FIGS. 5A and 5B. However, grasping surfaces 604a, 604b of the manipulator 600 connected with arms 602a, 602b each include pegs 640a, 640b and are spring biased by leaf springs 603a, 603b connected between respective pegs 604a, 604b and arms 602a, 602b. The grasping surfaces 604a, 604b are textured along their edges to resist slippage of tissue held therebetween. However, the texture differs from previous embodiments, and is shown to illustrate one of multiple different textures usable with the grasping surfaces 604a, 604b.

Figure 7A:
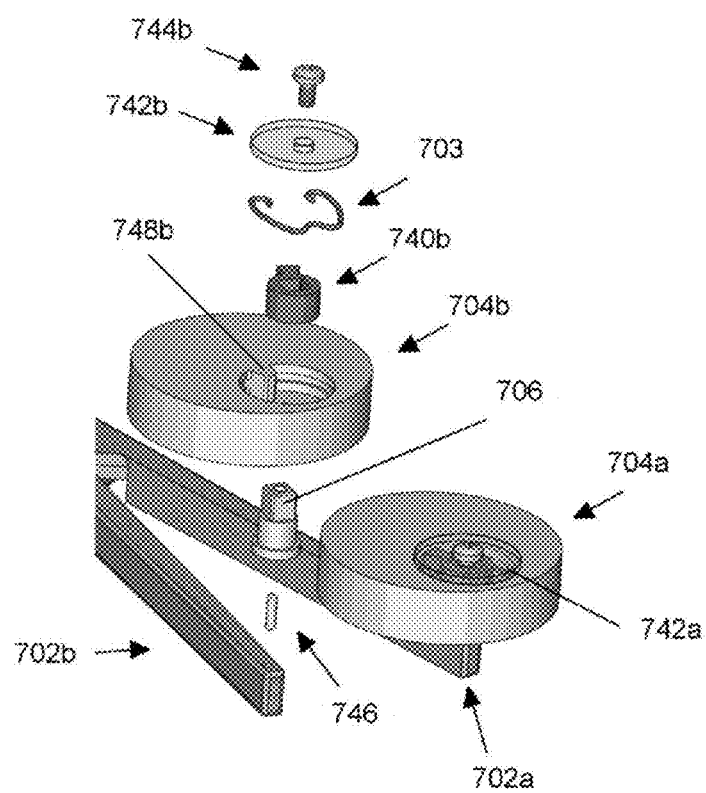
FIG. 7A is a partial exploded view and FIG. 7B is a top detail view of grasping surfaces of an alternative manipulator.
Figure 7B:
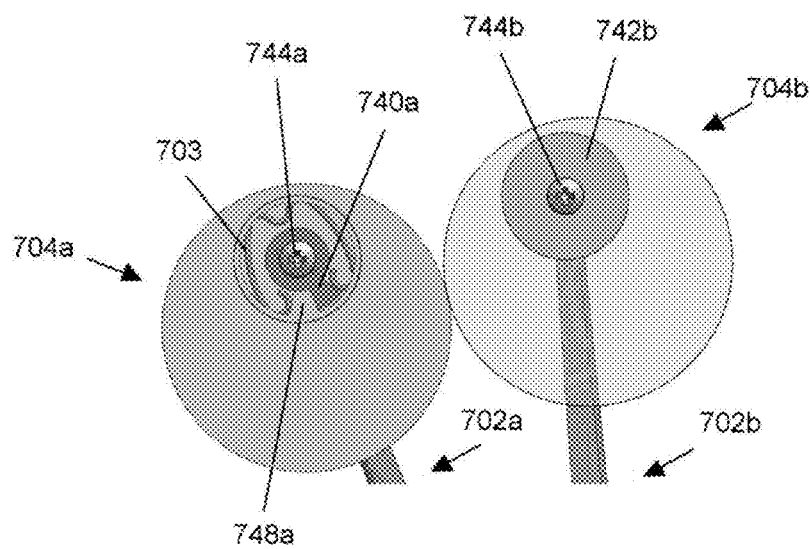
Figure 8A:
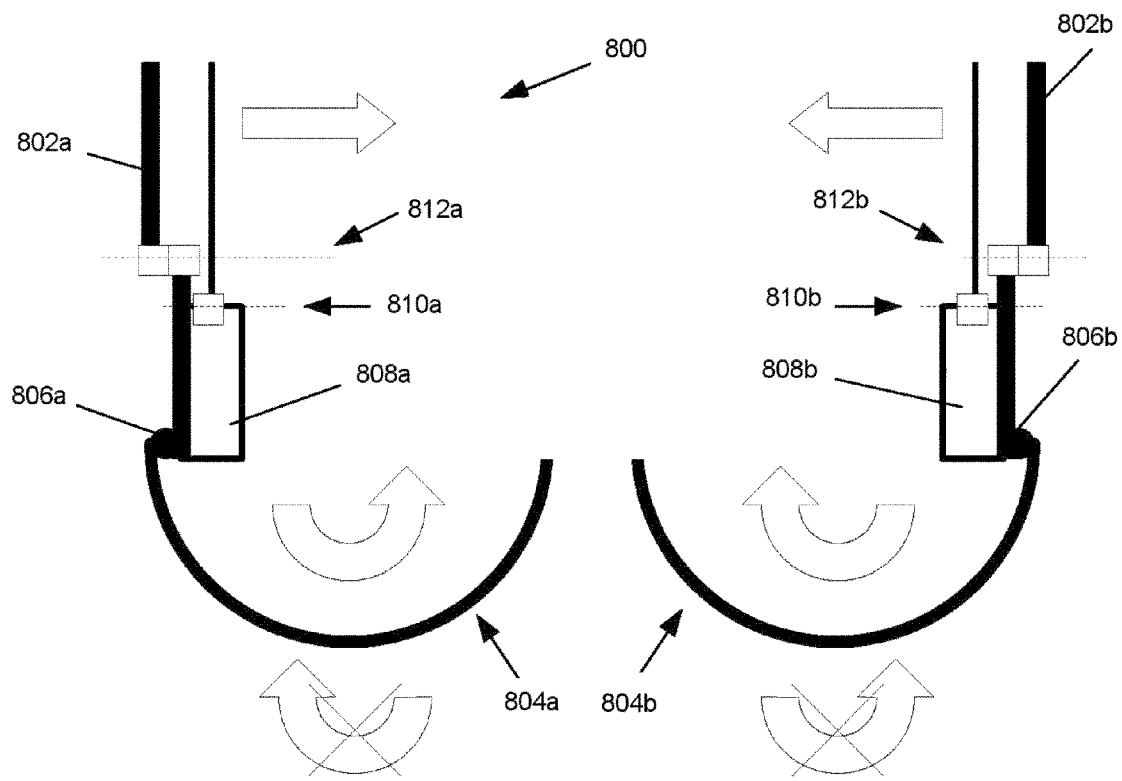
FIGS. 8A and 8B are partial top views of an alternative embodiment of a manipulator in accordance with the present invention in an open and closed configuration, respectively.
Figure 8B:
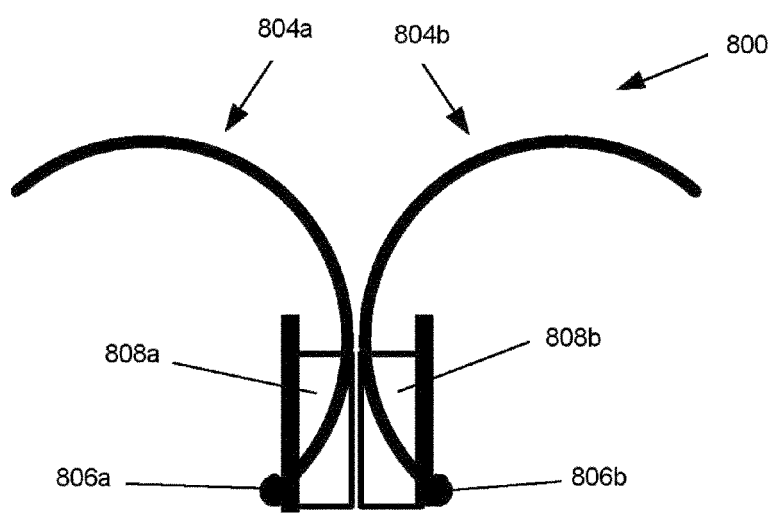

FIGS. 7A and 7B illustrate an alternative embodiment of a manipulator 700 in accordance with the present invention adapted for grasping and pulling tissues. The manipulator 700 resembles the manipulators 500, 600 of FIGS. 5 and 6. However, grasping surfaces 704a, 704b of the manipulator 700 are spring biased with a leaf spring 703 arranged in a cavity around the pivot point 706 at the end of respective arms 702a, 702b. The cavity has a stop 748a, 748b that contacts a key 740a, 740b which is biased by a spring 703a, 703b held within the cavity. Rotation of the grasping surfaces 704a, 704b is restricted in one direction by the stops 748a, 748b, and is resisted in the opposite direction by the springs 703a, 703b. As shown, the pivot points 706 are connected and are free rotate relative to respective arms 702a, 702b by a pin 746. The pivot points 706 are received within respective cavities of the grasping surfaces 704a, 704b. The cavities are sealed by caps 742a, 742b which are fixed in position by screws 744a, 744b or other fixation device. Note that the peg 746 and pivot point 706 are shown for only the right head, but the features are intended to be identical for the left head in this embodiment. Sealing the spring bias mechanism can, for example, reduce the amount of exposed moving parts of the manipulator thereby potentially increasing safety and prevent additional points of contamination accumulation during procedures FIGS. 8A and 8B illustrate an alternative embodiment of a manipulator 800 in accordance with the present invention. The manipulator 800 comprises a pair of arms 802a, 802b each of which is connected with a grasping surface 804a, 804b at a pivot point 806a, 806b. Each of the grasping surfaces 804a, 804b has a semi-circular shape that curves inward relative to the other grasping surface 804a, 804b. The grasping surfaces 804a, 804b are spring biased, and can be spring biased using any of the spring features described in embodiments described herein, or any other spring features that may be contemplated by one of ordinary skill in the art upon reflecting on the teachings presented herein. The manipulator 800 further comprises rigid grasping sections 808a, 808b each extending from a portion of a corresponding arm 802a, 802b. The manipulator can be useful, for example, in combination with endoscopes, enabling a strong, but rougher grasping of a large quantity of tissue.

Figure 8C:
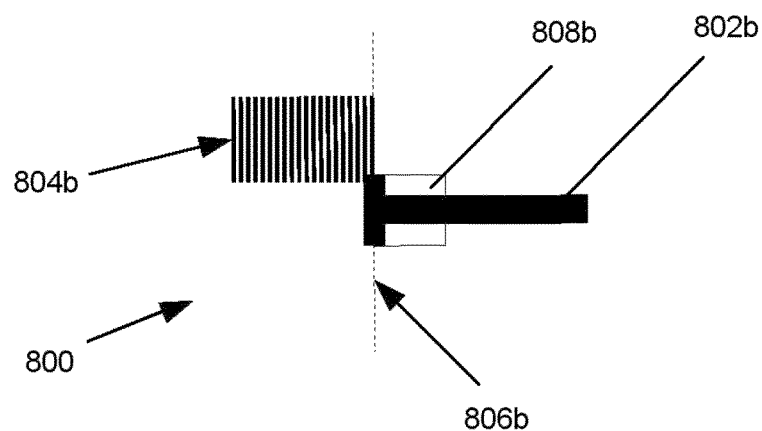
FIGS. 8C and 8D are side views of the manipulator of FIGS. 8A and 8B in an open and closed configuration, respectively.
Figure 8D:
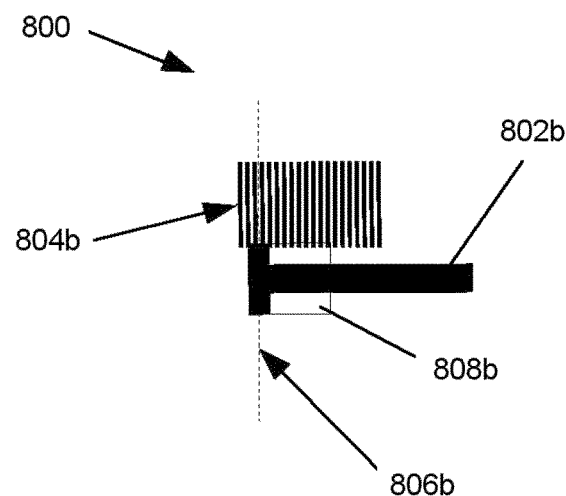

In FIG. 8A, the manipulator 800 is open, in that the grasping surfaces 804a, 804b are arranged to contact tissue for grasping. Once the grasping surfaces 804a, 804b are contacted to the target tissue, they are actuated by moving the arms 802a, 802b toward each other and urging the manipulator 800 toward the target tissue. As the arms 802a, 802b are moved closer together, the grasping surfaces 804a, 804b rotate at their pivot points 806a, 806b, grasping tissue and pulling tissue into the gap between the arms 802a, 802b. As the arms come together, the tissue is further contacted and captured by the rigid grasping sections 808a, 808b, which offer increased surface area for contacting the tissue, and which rigidly hold captured tissue in place. FIGS. 8C and 8D are side views of the manipulator 800 in an open and closed configuration, respectively. An offset can be seen between the grasping surfaces 804a, 804b and the grasping sections 808a, 808b that avoids physical interference between the grasping surfaces 804a, 804b and the grasping sections 808a, 808b when the manipulator 800 is actuated. Referring again to FIG. 8A, the arms 802a, 802b of the manipulator 800 are mechanically bendable about two pivot points. The arms 802a, 802b can be bent perpendicular to an axis of the arms 802a, 802b at a first pivot point 810a, 810b, i.e. into or out of the page from top to bottom. The arms 802a, 802b can also be bent about the axis of the arms 802a, 802b at a second pivot point 812a, 812b, i.e. into or out of the page from left to right. By mechanically bending the arms 802a, 802b, the grasping surfaces 804a, 804b can be arranged at a desired angle, including acute and obtuse angles.

Figure 9A:
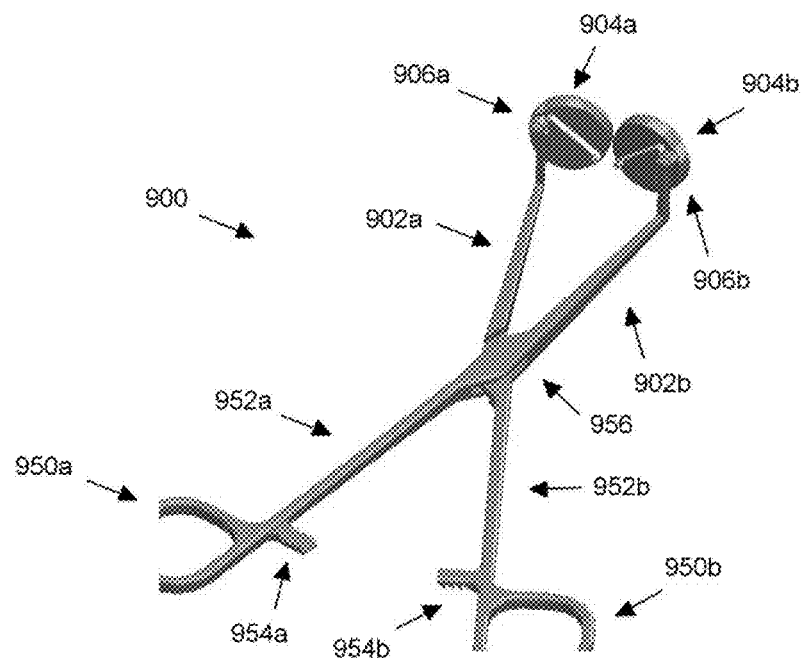
FIG. 9A is a perspective view of an alternative embodiment of a manipulator in accordance with the present invention.
Figure 9B:
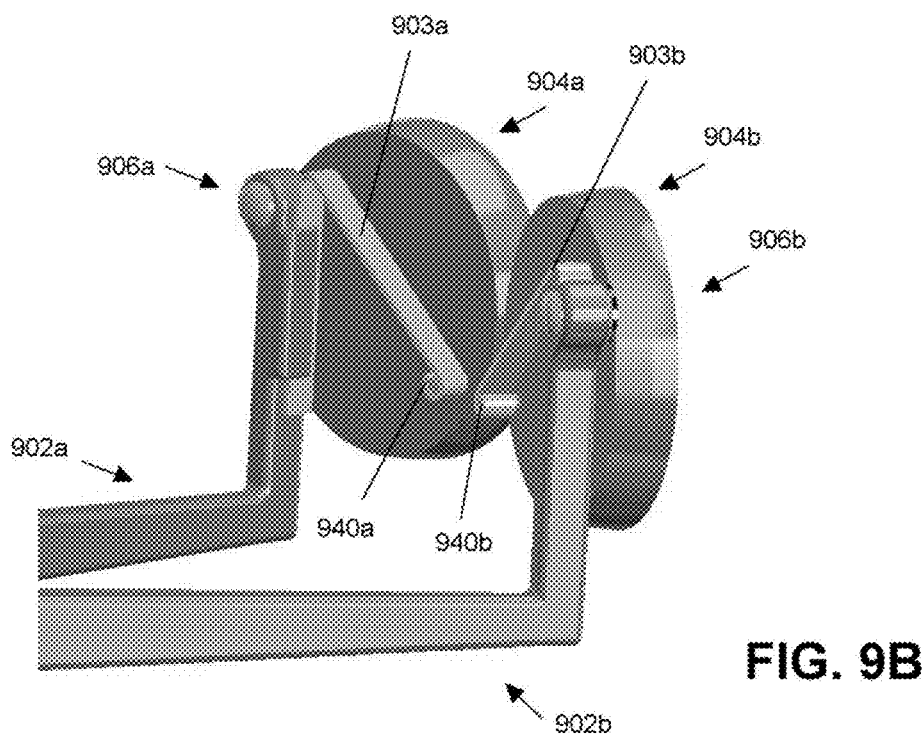
FIG. 9B is a detail view of the grasping surfaces of the manipulator of FIG. 9A.

FIGS. 9A and 9B illustrate an alternative embodiment of a manipulator 900 in accordance with the present invention adapted for grasping and pulling tissues. The manipulator 900 comprises a pair of arms 902a, 902b each of which is connected with a grasping surface 904a, 904b at a pivot point 906a, 906b. The distal portions of the arms 902a, 902b are angled at 90° from the proximal ends of the arms 902a, 902b and the levers 952a, 952b so that a user can access target tissue located at an angle relative to an incision, for example. In other embodiments, the distal portions of the arms can extend at a different angle relative to the proximal ends of the arms and/or the levers. The grasping surfaces 904a, 904b are rigid or semi-rigid surfaces which have a frustum shape. The frustum shape is intended to allow the edges of the grasping surfaces to mate along their surface, and accounts for the relative angle introduced by the geometry of the hinged arms 902a, 902b. For manipulators that are not actuated at a hinge, but rather include arms arranged parallel to each other during actuation the grasping surface can be cylindrical.

The grasping surfaces 904a, 904b each include pegs 940a, 940b and are spring biased by leaf springs 903a, 903b connected between respective pegs 904a, 904b and arms 902a, 902b. The springs 903a, 903b resist the grasping surfaces 904a, 904b, and by extension the pivot points 906a, 906b from being urged together. The pivot points 906a, 906b include shafts that allow the grasping surfaces 904a, 904b to pivot relative to the arms 902a, 902b. As above, the manipulator 900 further comprises levers 952a, 952b connected at a hinge 956 actuate the arms 902a, 902b when urged together. Proximal ends of the levers 952a, 952b includes finger loops 950a, 950b, and a locking mechanism 954a, 954b to allow the manipulator 900 to act as a clamp to fix tissue in place. Once the grasping surfaces 904a, 904b are contacted to the target tissue, the manipulator 900 can be actuated to draw tissue away from the target location. As with previous embodiments, when the manipulator 900 is released, the spring force of the springs 903a, 903b urge the grasping surfaces 904a, 904b to rotate in opposite directions, pushing the arms 902a, 902b apart to their original position.

Figure 10A:
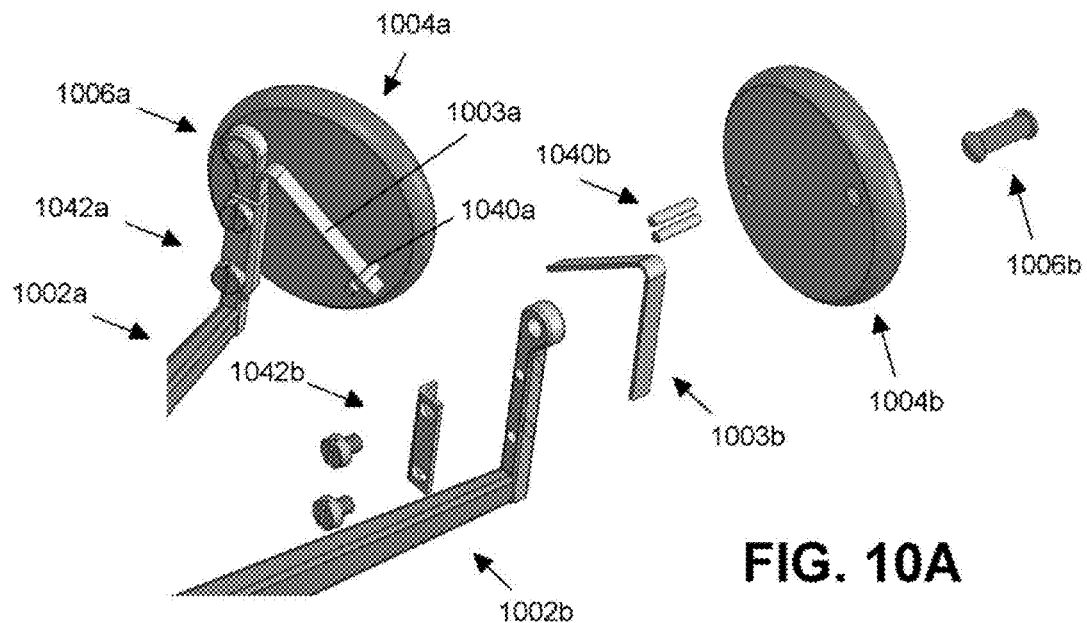
FIG. 10A is a partial exploded view of an alternative embodiment of a manipulator in accordance with the present invention.
Figure 10B:
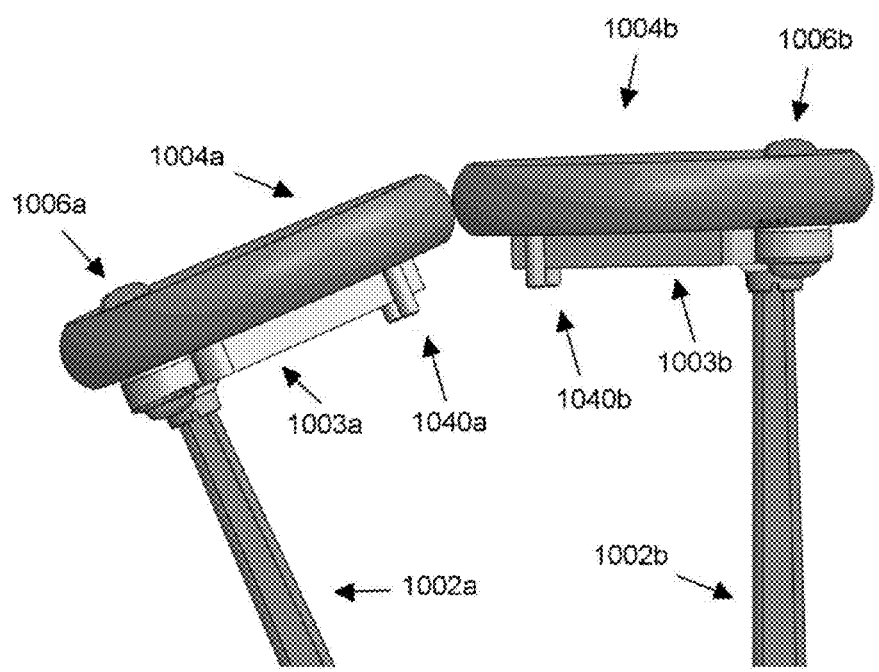
FIG. 10B is a top view of the grasping surfaces of the manipulator of FIG. 10A.

FIGS. 10A and 10B illustrate an alternative embodiment of a manipulator 1000 in accordance with the present invention adapted for grasping and pulling tissues. The manipulator 1000 resembles the manipulator 900 of FIGS. 9A and 9B. However, leaf springs 1003a, 1003b connected between two pings 1040a, 1040b and a bracket-and-screw 1042a, 1042b arrangement of the arms 1002a, 1002b. Upon reflecting on the teaching herein and the differences between the two embodiments, one of ordinary skill in the art will appreciate other mechanisms for exerting a spring force on the grasping surfaces 1004a, 1004b, all of which are contemplated and intended to be within the scope of the present invention. Further, as shown in FIG. 10B, the grasping surfaces 1004a, 1004b are rounded in shape along the edges to account for an angle introduced by the compound arms 1002a, 1002b. It can be useful when the distal portions of the arms 1002a, 1002b are angled at variable degrees relative to the proximal ends of the arms 1002a, 1002b and the levers, the rounded shape can allow the edges of the grasping surfaces 1004a, 1004b to mate along their surface. In some embodiments, the grasping ticket can be made from a more flexible material to allow the edges to at least partially flatten out against grasped tissue to increase surface contact.

FIGS. 11A-11D illustrate an alternative embodiment of a manipulator 1100 in accordance with the present invention. The manipulator 1100 comprises a pair of arms 1102a, 1102b each of which is connected with a grasping surface 1104a, 1104b at a pivot point 1106a, 1106b. Each of the grasping surfaces 1104a, 1104b has a semi-circular shape that curves inward relative to the other grasping surface 1104a, 1104b. The grasping surfaces 1104a, 1104b are spring biased, and can be spring biased using any of the spring features described in embodiments described herein, or any other spring features that may be contemplated by one of ordinary skill in the art upon reflecting on the teachings presented herein. The manipulator 1100 also includes a vein sealer 1108a, 1108b associated with the arms 1102a, 1102b.

Figure 11A:
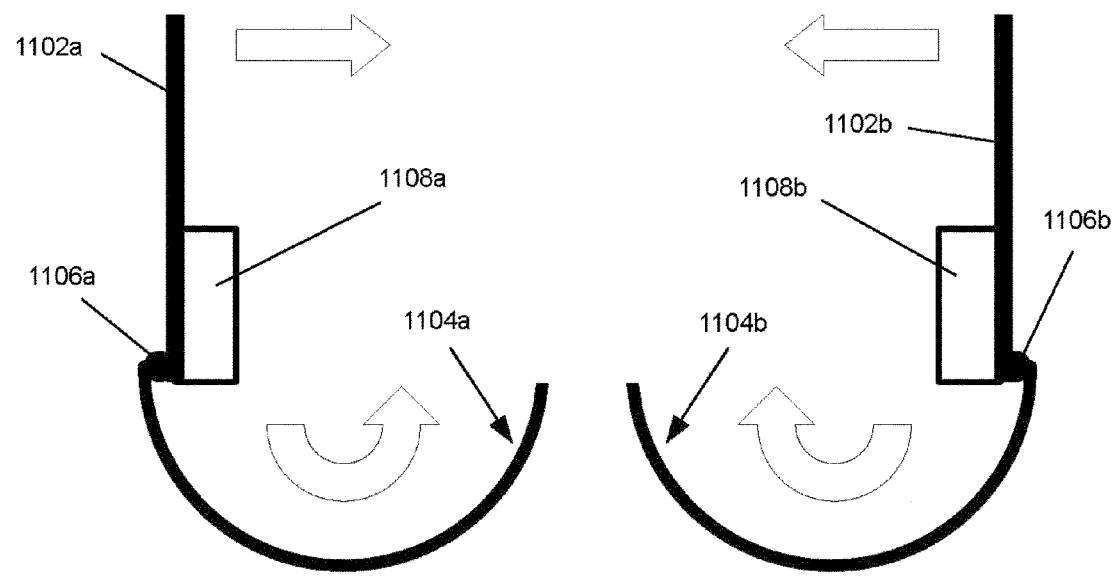
FIGS. 11A and 11B are partial end views of a further embodiment of a manipulator in accordance with the present invention in an open and closed configuration, respectively.

In FIG. 11A, the manipulator 1100 is open, in that the grasping surfaces 1104a, 1104b are arranged to contact tissue for grasping. Once the grasping surfaces 1104a, 1104b are contacted to the target tissue, they are actuated by moving the arms 1102a, 1102b toward each other and urging the manipulator 1100 toward the target tissue. As the arms 1102a, 1102b are moved closer together, the grasping surfaces 1104a, 1104b rotate at their pivot points 1106a, 1106b, grasping tissue and pulling tissue into the gap between the arms 1102a, 1102b. As the arms 1102a, 1102b come together, the vein sealer 1108a, 1108b can be activated to seal a vein. The vein sealer 1108a, 1108b can be, for example, a bipolar electrode pair, which destroys the tissue part in between, but can alternatively also be a clip applying pair of forceps, or some other mechanism. A manipulator 1100 having a vein sealer 1108a, 1108b as contemplated herein can be useful, for example, in endoscopic situations, where sealing veins lying in the deeper layers of cavity walls is necessary. Tissue can be grasped in one move and pulled into the manipulator, and the vein can be sealed without damaging the other deeper layers of the cavity walls. In addition, as with all other embodiments disclosed herein, the manipulator can include other therapeutic and/or diagnostic tools besides a vein sealer.

Figure 11B:
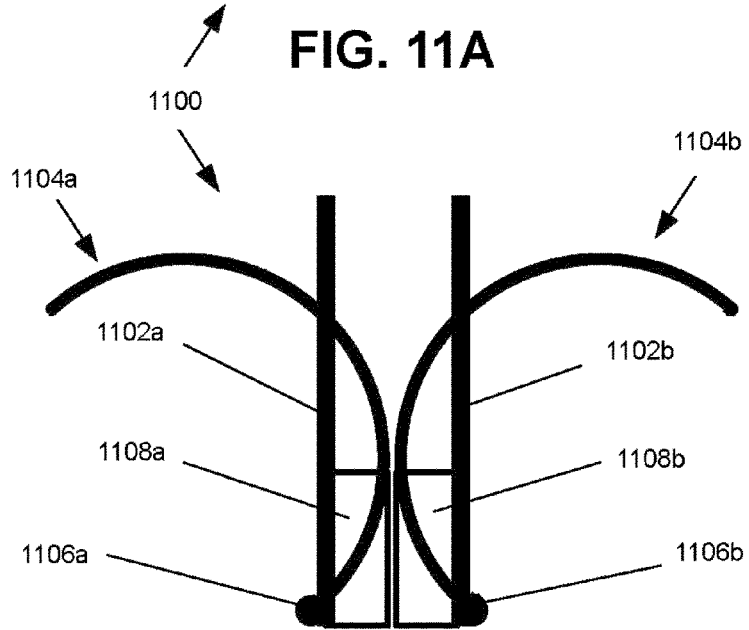
Figure 11C:
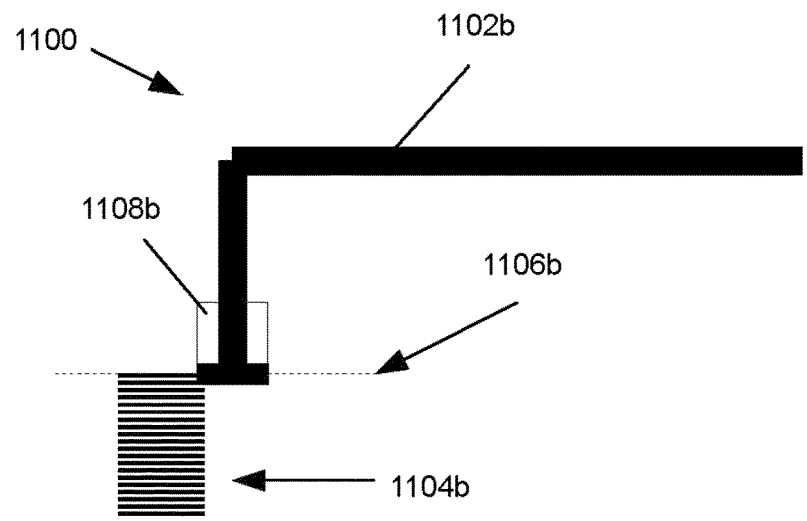
FIGS. 11C and 11D are side views of the manipulator of FIGS. 11A and 11B in an open and closed configuration, respectively.
Figure 11D:
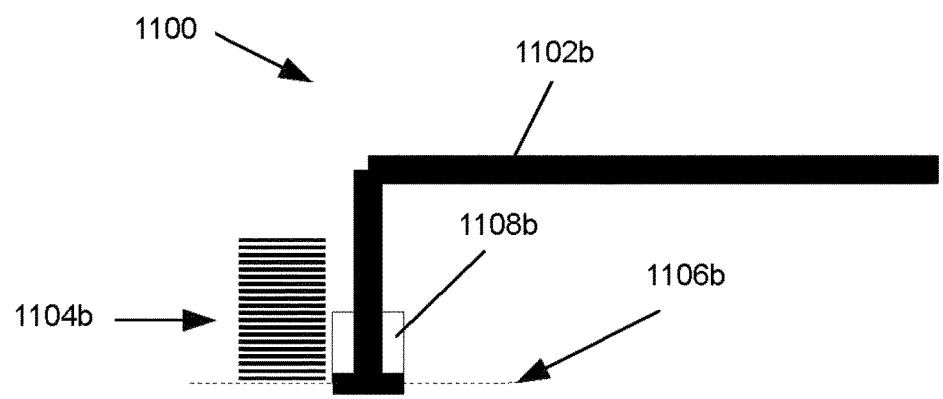

FIGS. 11C and 11D are side views of the manipulator 1100 in an open and closed configuration, respectively. An offset can be seen between the grasping surfaces 1104a, 1104b and the vein sealer 1108a, 1108b that avoids physical interference between the grasping surfaces 1104a, 1104b and the vein sealer 1108a, 1108b when the manipulator 1100 is actuated. As shown, the arm 1102a, 1102b of the manipulator 1100 has a perpendicular bend so that the manipulator 1100 can approach the target tissue in a direction substantially parallel to the surface of the target tissue. The arm of the manipulator can alternatively form an obtuse or acute angle. In this way, sequences requiring several complex manipulations can be replaced with a single move.

Figure 12:
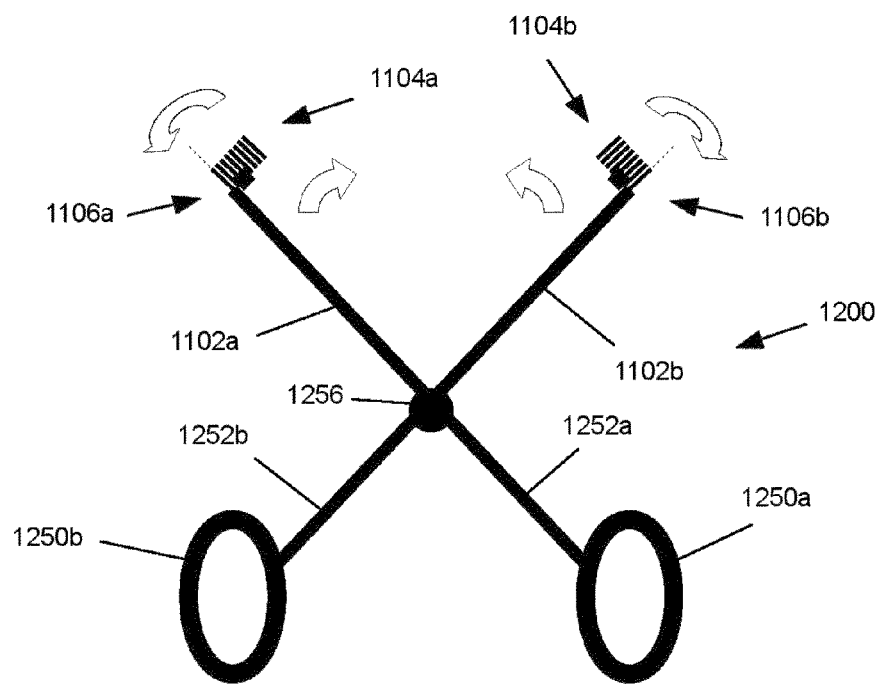
FIG. 12 is a top view of a manipulator comprising the arms and grasping surfaces of FIGS. 11A-11D in an open configuration.

FIG. 12 is a top view of a manipulator 1200 comprising the arms and grasping surfaces of FIGS. 11A-11D in an open configuration. The manipulator 1200 comprises a pair of arms 1102a, 1102b have a perpendicular bend and are connected together at a pivot 1256 and having levers 1252a, 1252b for actuation of the arms 1102a, 1102b. Proximal ends of the levers 1252a, 1252b includes finger loops 1250a, 1250b. Each of the arms 1102a, 1102b is connected with a grasping surface 1104a, 1104b at a pivot point 1106a, 1106b. The grasping surfaces 1104a, 1104b are actuated to pivot perpendicular to the arms (i.e., in the plane of the page). A user actuates the manipulator 1200 using the handles 1252a, 1252b. As the arms 1102a, 1102b approach each other the grasping surfaces 1104a, 1104b rotate about a shaft at the pivot point 1106a, 1106b. Each shaft is aligned along the corresponding arm 1102a, 1102b so that the grasping surfaces 1104a, 1104b rotate perpendicular to the arms 1102a, 1102b.

Figure 13:
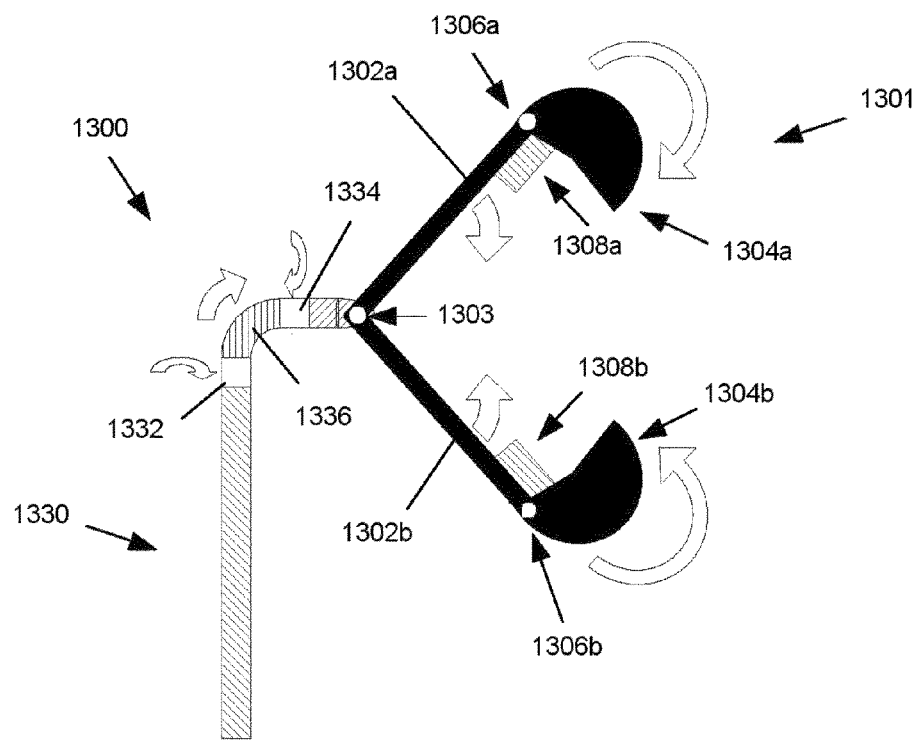
FIG. 13 is a side view of an endoscope for use with embodiments of manipulators in accordance with the present invention.

FIG. 13 illustrates a further embodiment of a manipulator 1300 in accordance with the present invention comprising a single primary arm 1330. The arm 1330 includes two location joints 1332, 1334 that allow a head 1301 of the manipulator 1300 to rotate in one or two axes and a bending joint 1336 that allows the head 1301 to bend so that the head is aligned at an angle relative to an axis defined by the arm 1302. The head 1301 comprises a pair of smaller arms 1302a, 1302b pivotally connected with each other at a main pivot point 1303. Each of the arms 1302a, 1302b is connected with a grasping surface 1304a, 1304b at a pivot point 1306a, 1306b. The manipulator 1300 also includes a vein sealer 1308a, 1308b portions of which extend from each arm 1302a, 1302b. Although in other embodiments, the manipulator can include some other therapeutic and/or diagnostic tool.

The arms 1302a, 1302b can be urged together at the pivot point 1303 connecting them. The grasping surfaces 1304a, 1304b are actuated as the arms 1302a, 1302b are urged together. The grasping surfaces 1304a, 1304b grasp tissue and pull tissue into the gap between the arms 1302a, 1302b. As the arms 1302a, 1302b come together, the vein sealer 1308a, 1308b penetrates the tissue to seal a vein.

Figure 14A:
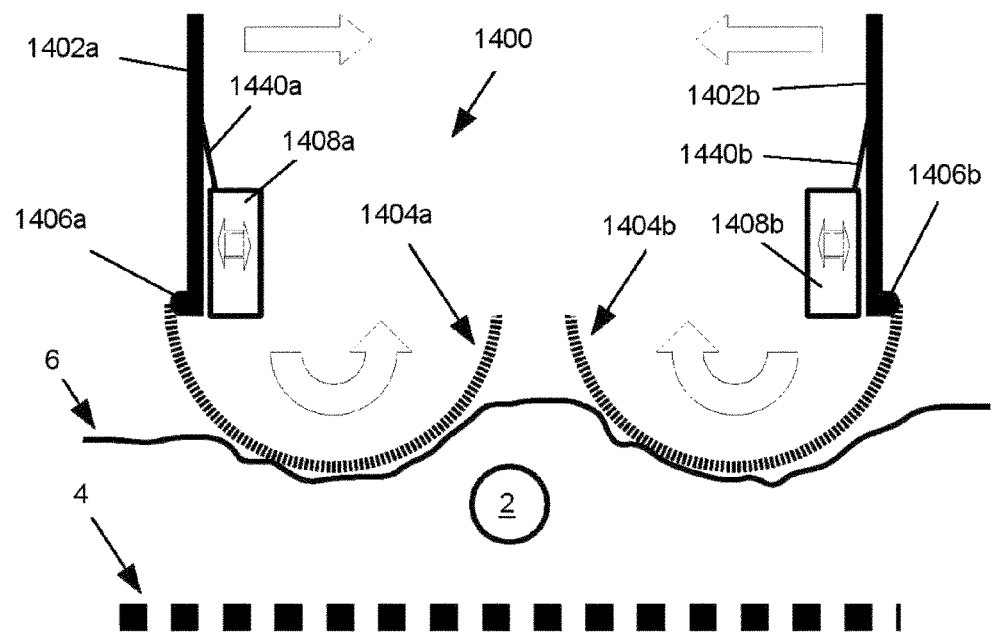
FIGS. 14A and 14B are partial top view of a still further embodiment of a manipulator in accordance with the present invention engaging tissue and isolating a vein.
Figure 14B:
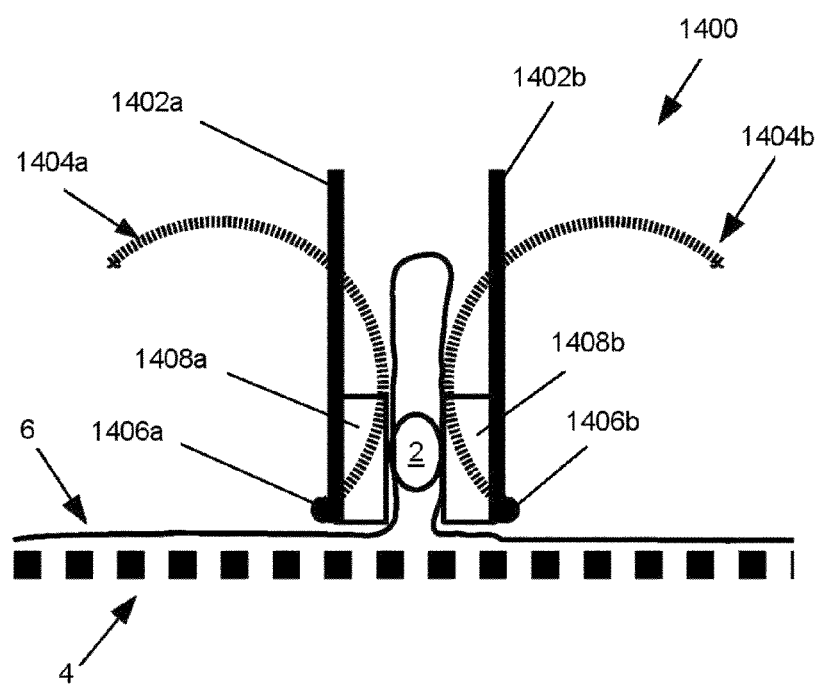

FIGS. 14A and 14B illustrate a further embodiment of a manipulator 1400 in accordance with the present invention similar to the embodiment of FIGS. 11A and 11B, but having a vein sealer 1408a, 1408b applied to target tissue to seal a vein. The manipulator 1400 comprises a pair of arms 1402a, 1402b each of which is connected with a grasping surface 1404a, 1404b at a pivot point 1406a, 1406b. Each of the grasping surfaces 1404a, 1404b has a semi-circular shape that curves inward relative to the other grasping surface 1404a, 1404b. The manipulator 1400 also includes the vein sealer 1408a, 1408b, but unlike in previous embodiments, the portions are connected to each arm 1402a, 1402b by additional, flexible or semi-flexible arms 1440a, 1440b that can enable the vein sealer 1408a, 1408b to function in a semi-closed state of the manipulator 1400, for example. As with other embodiments, the manipulator can include some other therapeutic and/or diagnostic tool.

In FIG. 14A, the manipulator 1400 is open, and the grasping surfaces 1404a, 1404b are pressed against the tissue 6 at the target site with the vein 2 arranged between the grasping surfaces 1404a, 1404b. As the arms 1402a, 1402b are urged together, the grasping surfaces 1404a, 1404b engage the tissue until the resistance of the tissue between the grasping surfaces 1404a, 1404b overcomes a spring bias so that the grasping surfaces 1404a, 1404b begin to pivot inward. As the grasping surfaces 1404a, 1404b pivot inward, tissue is drawn between the arms 1402a, 1402b of the manipulator 1400. As the arms 1402a, 1402b are further urged together and urged closer to muscle 4, the grasping surfaces 1404a, 1404b continue to grasp and pull tissue into the gap between the arms 1402a, 1402b. As can be seen in FIG. 14B, a contact surface of the tissue 14 is drawn inward as the head of the manipulator 1400 is urged toward the muscle 4 and the vein 2 is arranged between the vein sealer 1408a, 1408b portions. The vein sealer 1408a, 1408b can then seals the vein 2. (For example, where the vein sealer includes a pair of electrodes, the electrodes can be fired.)

Figure 15:
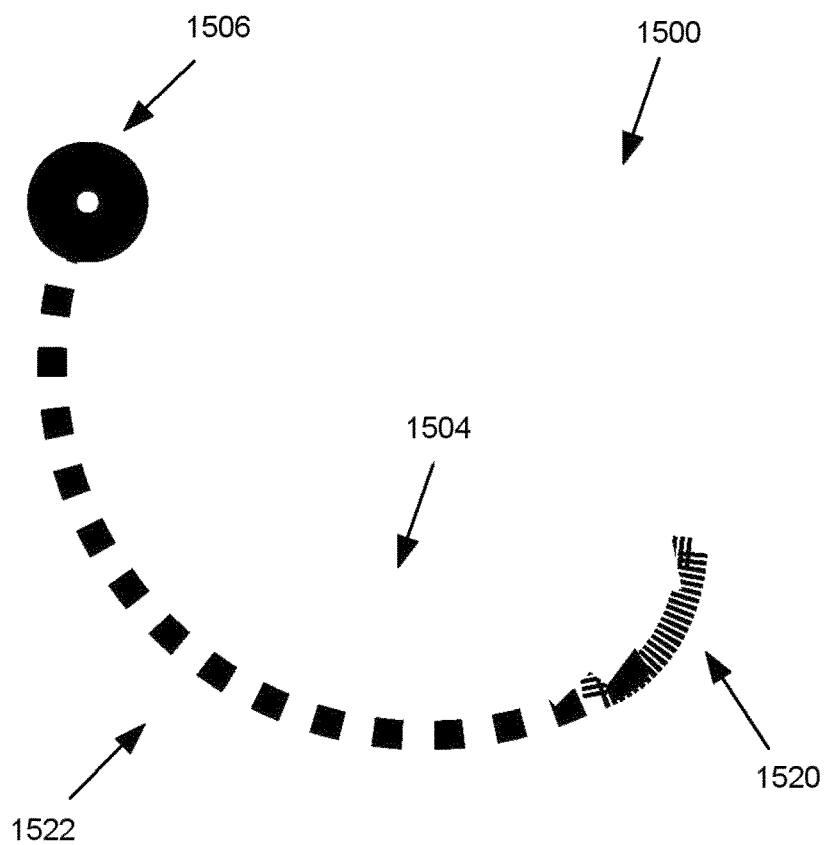
FIG. 15 is a schematic view of the grasping surface for use with embodiments of manipulators in accordance with the present invention.

FIG. 15 is an isolated schematic view of a grasping surface 1500 for use with embodiments of manipulators in accordance with the present invention. The grasping surface 1500 extends in a semi-elliptical shape away from a pivot point 1506. The distal portion 1520 of the grasping surface 1500 has a texture that is designed for grasping, while the main section 1522 trailing the distal portion 1520 to a proximal end has a texture that is designed for pulling tissue in.

Figure 16:
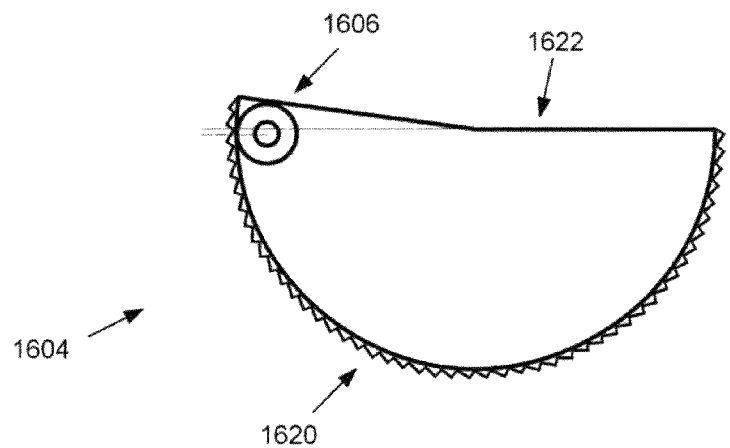
FIGS. 16, 17, and 18 are detailed views of varying grasping surfaces usable with embodiments of manipulators in accordance with the present invention.
Figure 17:
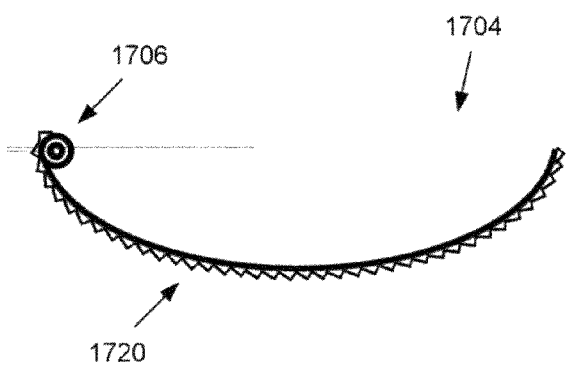
Figure 18:
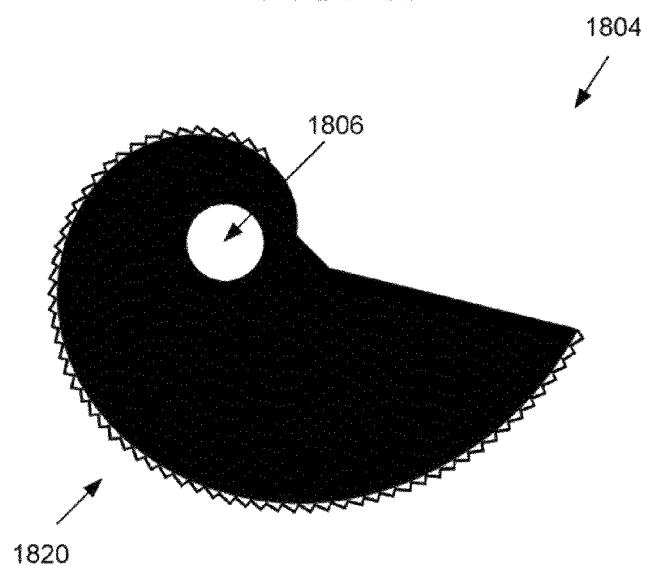

FIGS. 16-18 illustrate additional, detail views of different grasping surfaces 1604, 1704, 1804 for use with embodiments of manipulators in accordance with the present invention. Referring to FIG. 16, the rolling section 1604 has varying width with the distal and proximal ends of the rolling section 1604 substantially connected by a back edge 1622 that is not textured and has a slightly compound angle. The grasping edge 1620 of the rolling section 1604 is toothed, with the teeth biased in the direction towards pulling-in. The bias of the teeth toward pulling-in encourages the grasping surface to grab target tissue when actuating the manipulator to a closed position, while substantially avoiding grabbing tissue when the manipulator is released or actuated to an open position. The rotation shaft 1606 is farther in than the edge of the grasping surface 1604. Referring to FIG. 17, the grasping surface 1704 resembles previously described grasping surfaces in that its width is generally consistent along the grasping surface 1704. A grasping edge 1720 of the rolling section 1704 is toothed, with the teeth biased in the direction towards of pulling-in. The rotation shaft 1706 is farther in than the edge of the grasping surface 1700. Referring to FIG. 18, the rolling section 1804 has varying width and the grasping edge 1820 is shaped in a spiral. The grasping edge 1820 of the rolling section 1804 is toothed, with the teeth biased in the direction towards of pulling-in. The rotation shaft 1806 is even farther in than the edge of the grasping surface 1804 than the previous grasping surfaces.

FIGS. 19A-19C illustrate a further grasping surface for use with embodiments of manipulators in accordance with the present invention. FIGS. 19A and 19B are partial top views of a grasping surface 1904 connected with an arm 1902. The grasping surface 1904 is semi-circular in shape. The grasping surface 1904 is not connected to the arm 1902 by a shaft. Rather, the grasping surface 1904 bends at a pivot point 1906, similar to the embodiment of FIGS. 1A-1I. The distal end of the grasping surface 1904 is connected to the proximal end of the grasping surface 1904 by a brake and plate spring 1924. When the grasping surface 1904 is actuated, the brake and plate spring 1924 resists collapse of the grasping surface 1904, and helps return the grasping surface 1904 to the unactuated position. The manipulator of FIGS. 19A-19C further comprises a rigid grasper 1908. As can be seen in the side view of FIG. 19C, the rigid grasper 1908 is offset from the grasping surface 1904.

Figure 20A:
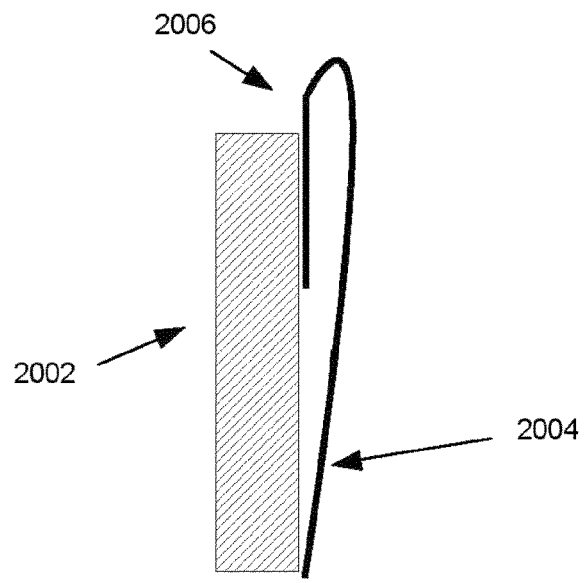
FIGS. 20A and 20B are partial top views of an alternative embodiment of a manipulator in accordance with the present invention in a closed and open configuration, respectively.
Figure 20B:
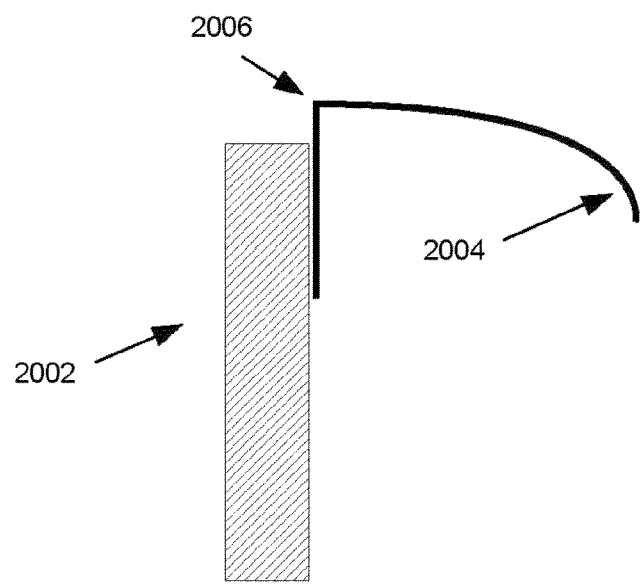
Figure 21A:
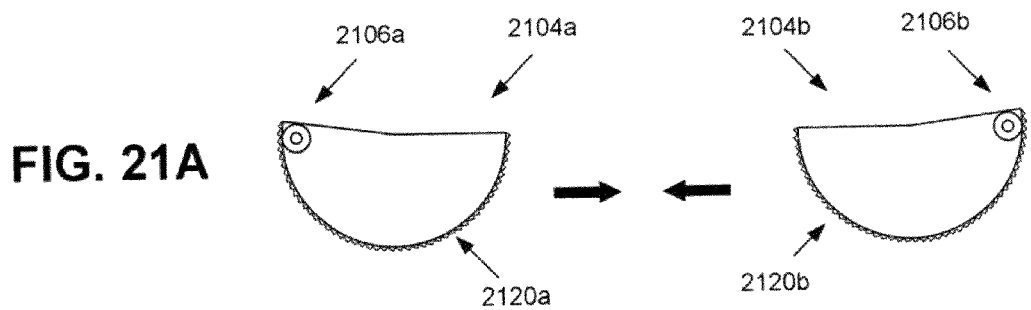
FIGS. 21A-21E illustrate advancement of a grasping surface for use with embodiments of manipulators in accordance with the present invention as the manipulator arms are closed.
Figure 21B:
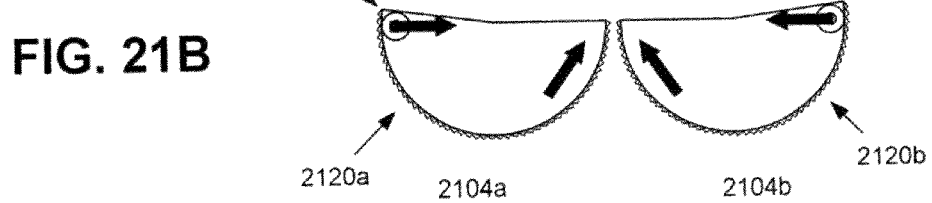
Figure 21C:
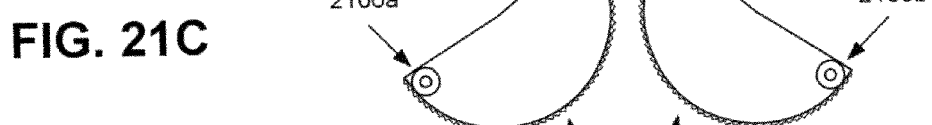
Figure 21D:
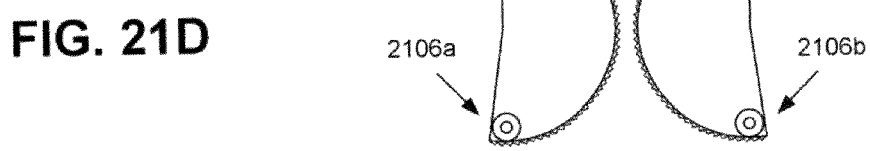
Figure 21E:
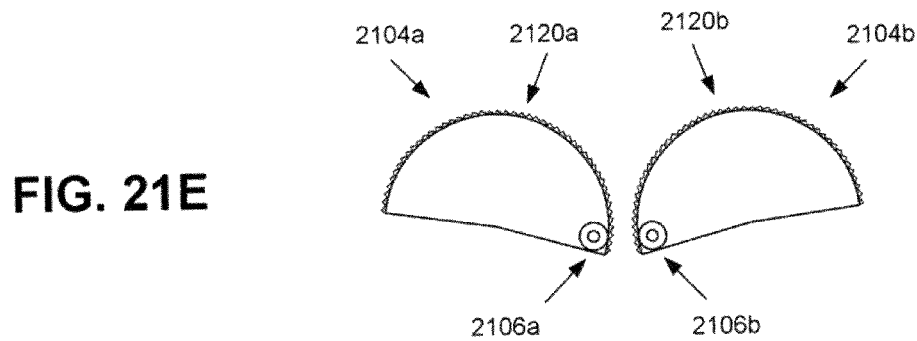

FIGS. 20A and 20B are partial top views illustrating a further grasping surface 2004 for use with embodiments of manipulators in accordance with the present invention. The grasping surface 2004 is connected with an arm 2002, and as above bends at a corner 2006, rather than rotating. The grasping surface 2004 is semi-parabolic in shape; however there is no brake and plate spring, and the grasping surface 2004 is bendable so that the grasping surface 2004 is urged substantially against the arm 2002. The grasping surface 2004 pressed to the arm 2002 can even be deformed, by means of which the diameter of the manipulator can be decreased during leading, substantially reducing or avoiding the offset of some embodiments, such as the embodiment shown in FIG. 1.

The geometric shape of the grasping surfaces of FIGS. 19A-20B can be of several types, taking into consideration that the pivot points are farther and farther from the rotation angle made up by the joint have to be located farther from the rotation angle in the moment of grasping.

FIGS. 21A-21E illustrate actuation of a pair of the grasping surfaces 2104a, 2104b of FIG. 21. As the pivot points 2106a, 2106b of the grasping surfaces 2104a, 2104b are urged together and the grasping edges 2120a, 2120b of the grasping surfaces 2104a, 2104b engage tissue, the grasping surfaces 2104a, 2104b are pivoted at the pivot points 2106a, 2106b so that the tissue can be into the manipulator by teeth of the grasping edges 2120a, 2120b. The teeth draw in the tissue and advance the tissue into the manipulator 2100 so that the target can be acted on. For example, the target may be a vein, and the manipulator may be actuated to seal the vein.

While the previous embodiments have described manipulators having grasping surfaces that are usable to grasp and pull tissue toward the manipulator, in still other embodiments manipulators having grasping surfaces that urge thread and other materials outward and away from the manipulator and outward toward a target.

Figure 22A:
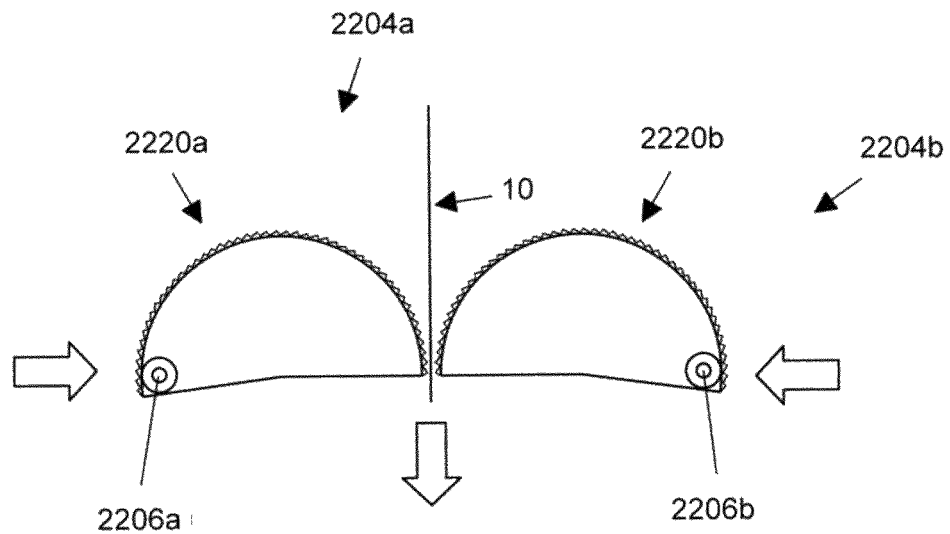
FIGS. 22A and 22B are partial top views of an embodiment of a manipulator in accordance with the present invention for advancing a thread along an axis.
Figure 22B:
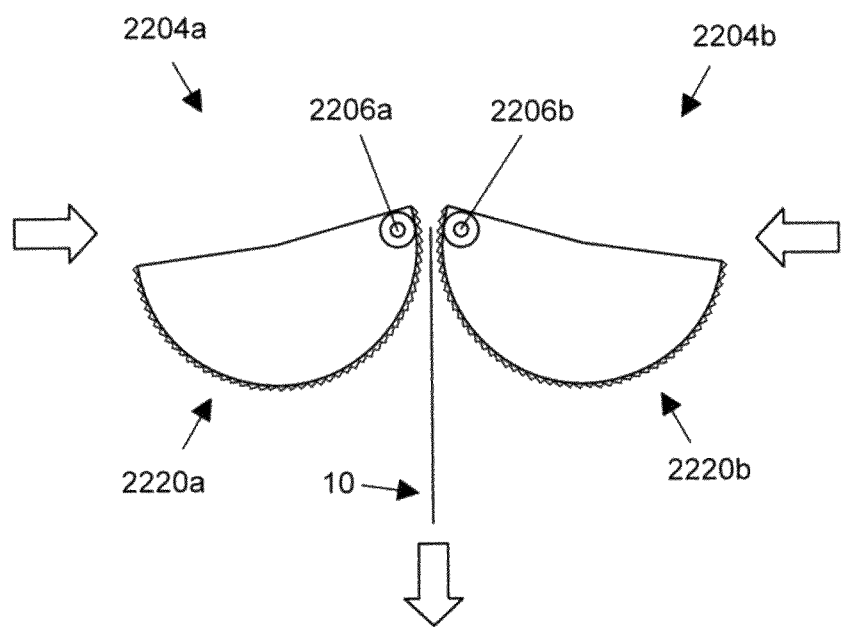

FIGS. 22A and 22B are partial top views illustrating grasping surfaces 2204 for use with embodiments of manipulators in accordance with the present invention to urge thread 10, wire, or any target object outward and away from the manipulator. When the rotations shafts 2206a, 2206b of the grasping surfaces are urged together, the grasping surface 2204a, 2204b are pivoted downward toward the bottom of the page. The grasping edge 2220a, 2220b has teeth or any other structure or texture pattern that can grasp the thread 10 and urge it downward of the page so that the thread 10 is advanced away from the manipulator.

Figure 23A:
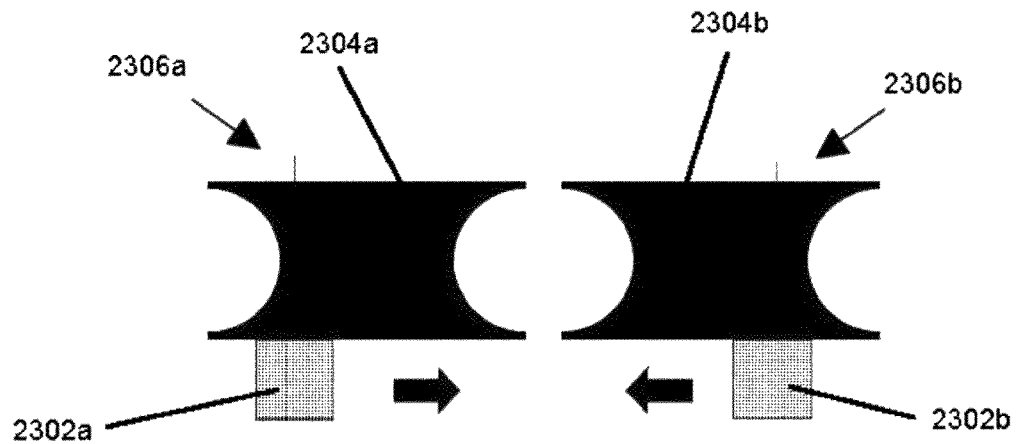
FIGS. 23A and 23B are partial end views of an embodiment of a manipulator in accordance with the present invention for advancing a thread along an axis.
Figure 23B:
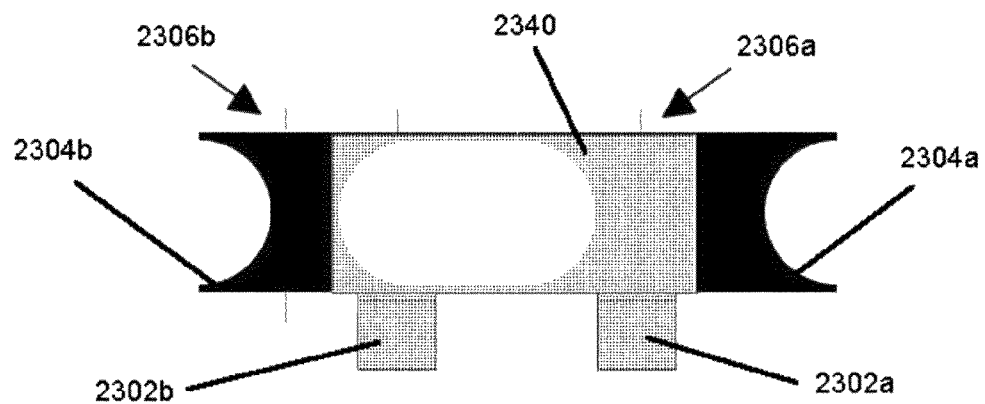

FIGS. 23A and 23B are partial end views of an embodiment of a manipulator 2300 in accordance with the present invention for advancing a thread along an axis. The grasping surfaces 2304a, 2304b are circular in shape and grooved. The grasping surfaces 2304a, 2304b are connected with arms 2302a, 2302b of the manipulator 2300 and have pivot points 2306a, 2306b that are off-center so that the grasping surfaces 2304a, 2304b are cammed in their motion. As shown in FIG. 23B, a line guide 2340 feeds a thread or line between the grasping surfaces 2304a, 2304b to prevent binding.

Figure 23C:
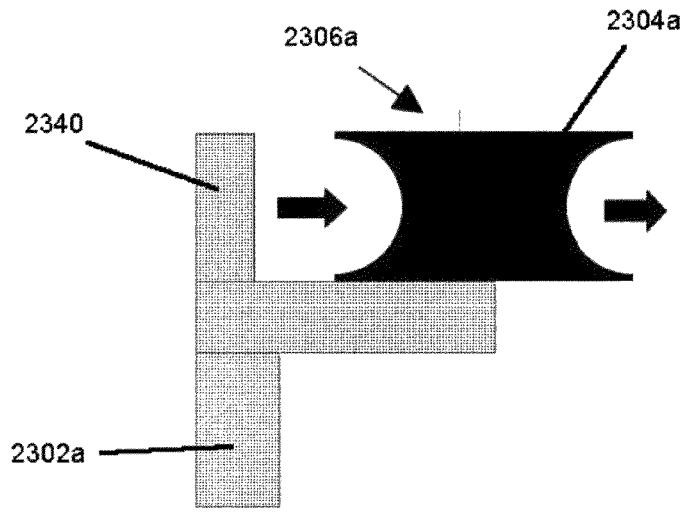
FIG. 23C is a partial side view of the manipulator of FIGS. 23A and 23B.
Figure 23D:
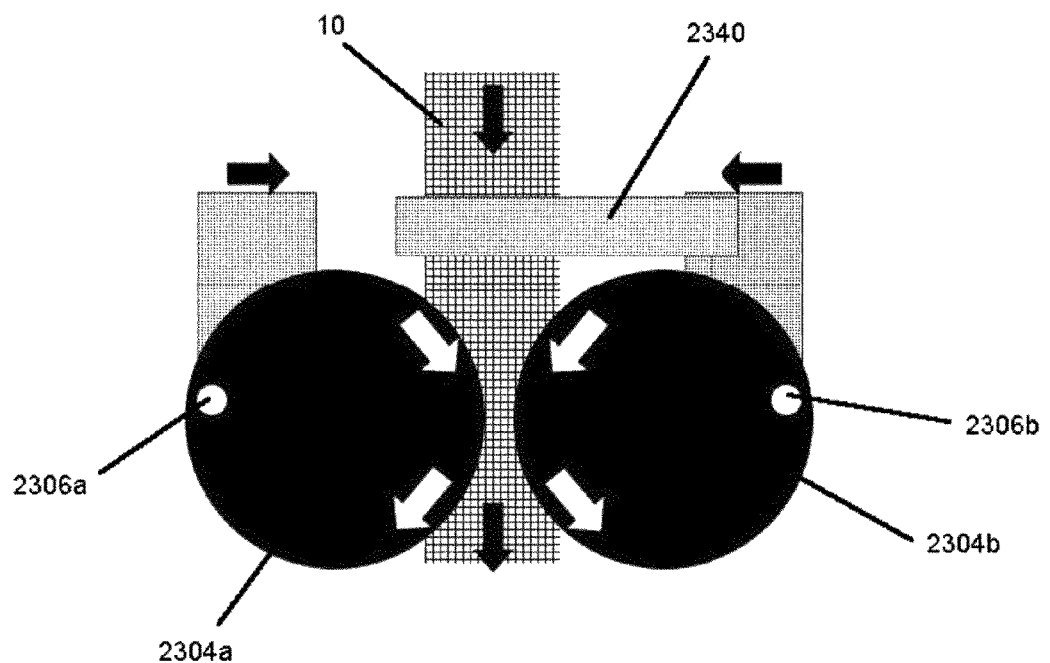
FIG. 23D is a partial top view of the manipulator of FIGS. 23A-23C.
Figure 24A:
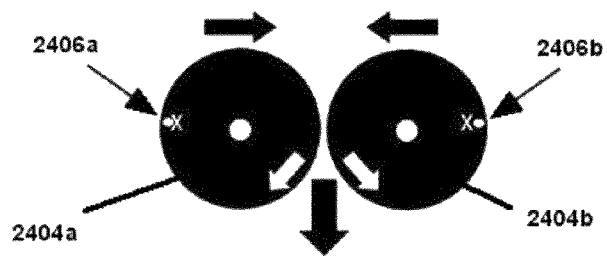
FIGS. 24A-24D illustrate incremental advancement of a target using embodiments of grasping surfaces for use with manipulators in accordance with the present invention.
Figure 24B:
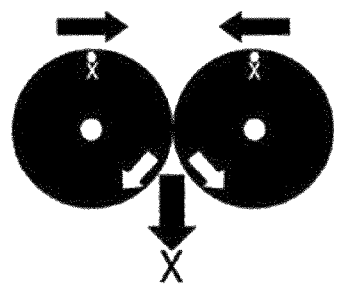
Figure 24C:
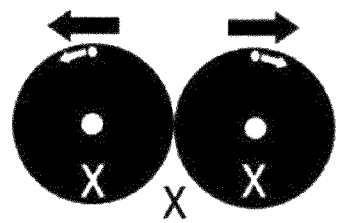
Figure 24D:
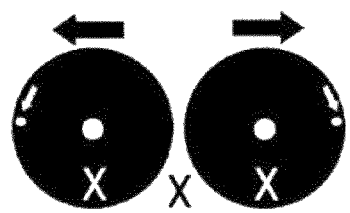
Figure 25A:
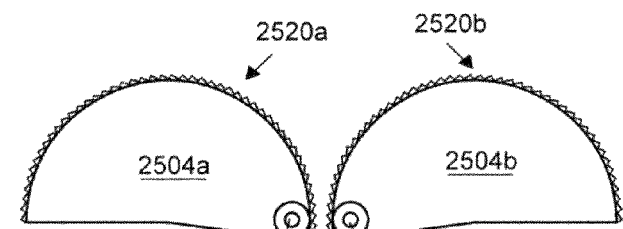
FIGS. 25A-25E illustrate an alternative embodiment of a grasping surface for use with embodiments of manipulators in accordance with the present invention and incremental advancement of the grasping surface adjust the size of a tube.
Figure 25B:
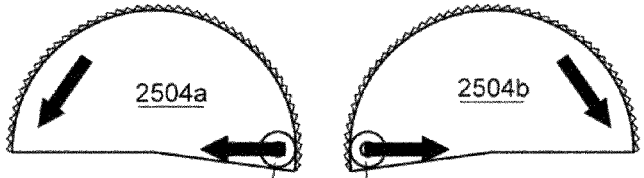
Figure 25C:
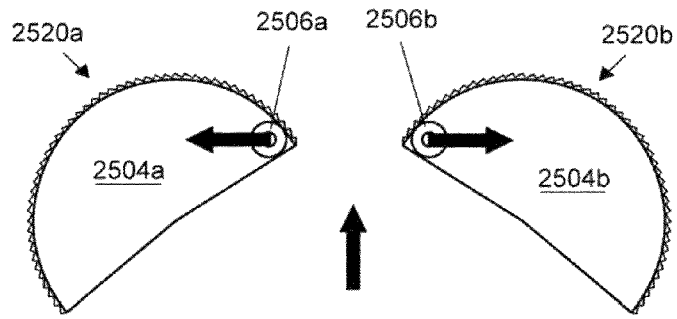
Figure 25D:
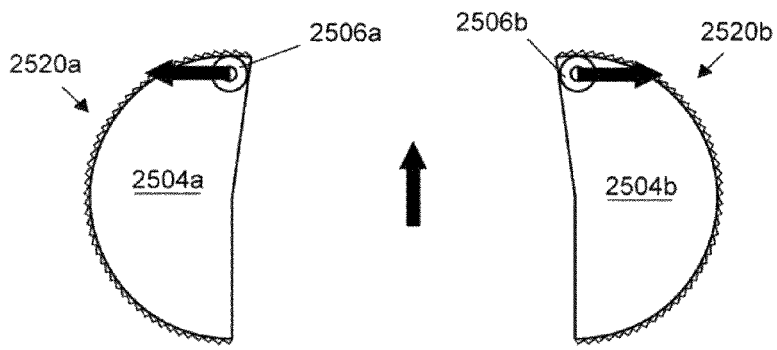
Figure 25E:
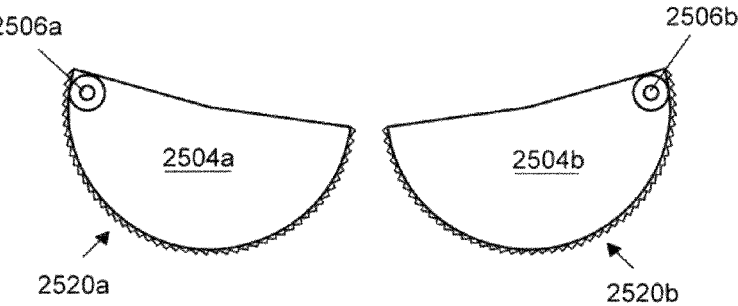
Figure 26A:
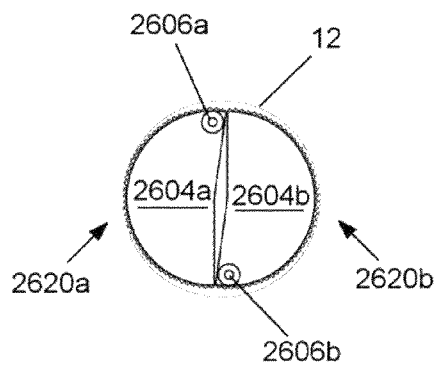
FIGS. 26A-26D illustrate a further embodiment of a grasping surface for use with embodiments of manipulators in accordance with the present invention and incremental advancement of the grasping surface within a tube.
Figure 26B:
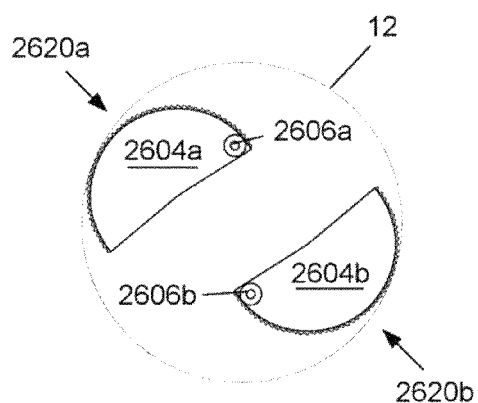
Figure 26C:
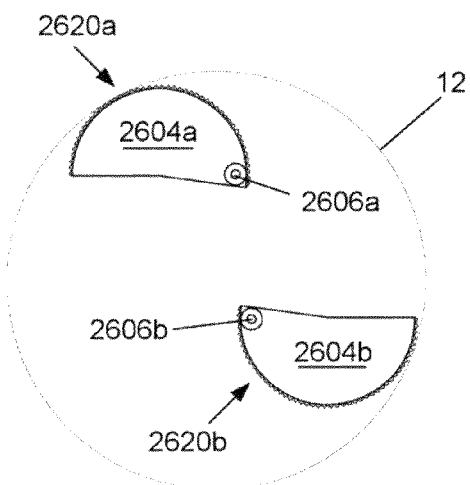
Figure 26D:
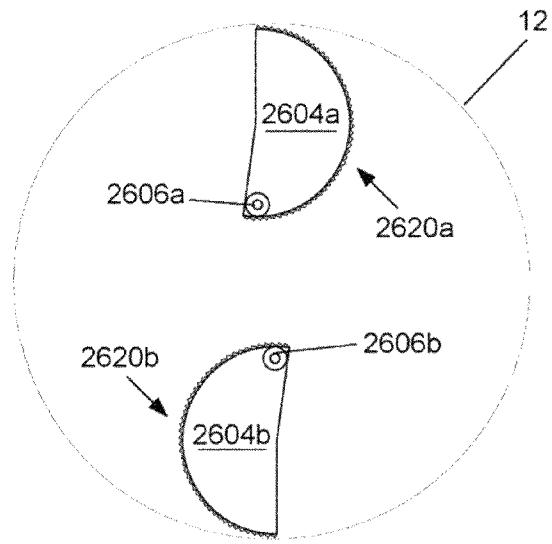

FIG. 23C is a side view of the manipulator 2300 of FIGS. 23A and 23B showing the line guide 2340 and a grasping surface 2304a relative to an arm 2302a of the manipulator 2300. Referring to FIG. 23D, when the arms 2302a, 2302b are urged together the grasping surfaces 2306a, 2306b are rotated, drawing a line or thread 10 through the line guide 2340 and outward of the manipulator 2300.

FIGS. 24A-24D illustrate incremental advancement of grasping surfaces 2404a, 2404b for use with embodiments of manipulators in accordance with the present invention to advance a target, such as a thread, as the manipulator arms are closed. The pivot points 2406a, 2406b in the circular grasping surfaces can move one way in a circular groove. When the pivot point is stopped it is signed with 'x', when it's moving it is signed with a small arrow. Opening and closing the manipulator are signed with large horizontal arrows above the grasping surfaces. Movement of the target arranged between the grasping surfaces is signed with a large vertical arrow. When target movement is stopped, it is signed with an 'X' below the grasping surfaces. The embodiment of FIGS. 24A-24D is similar to that of FIGS. 23A-23D, until the manipulator is in a closed configuration. The manipulator can then be opened with the grasping surfaces remaining sufficiently closed and motionless such that the target is held in position, but the pivot points move in their circular grooves to the position of FIG. 24A. The manipulator can then advance the target again. The grasping surfaces can incrementally advance a target or other object while retaining some grasping force to resist retreat of the target. The advancement resembles that when using a ratchet. The grasping surfaces roll only one way, but do not pull back the target.

In still other embodiments manipulators having grasping surfaces that perform other tasks to assist the manipulator are contemplated. For example, FIGS. 25A-25E illustrate a pair of further grasping surfaces 2504a, 2504b for use with embodiments of manipulators in accordance with the present invention and actuation of the pair of the grasping surfaces 2504a, 2504b. The pivot points 2506a, 2506b of the grasping surfaces 2504a, 2504b are arranged proximate to one another in the unactuated position, with the grasping edges 2520a, 2520b operating so that they rotate away from each other. This motion allows the manipulator to be used within a predefined operating space. Such manipulators can, for example, be advanced through a tube having a known or unknown diameter.

FIGS. 26A-26D illustrate a pair of further grasping surfaces 2604a, 2604b for use with embodiments of manipulators in accordance with the present invention arranged within a tube 12 with the back edges of the grasping surfaces 2604a, 2604b against each other. As the grasping surfaces 2604a, 2604b are rotated about a pivot point 2606a, 2606b at their respective distal ends, the grasping edges 2620a, 2620b push outward to expand the diameter of the tube 12. The expanded tube can increase access to a target site, improve flow through the tube, allow introduction of tools or other tubes, etc.

Figure 27A:
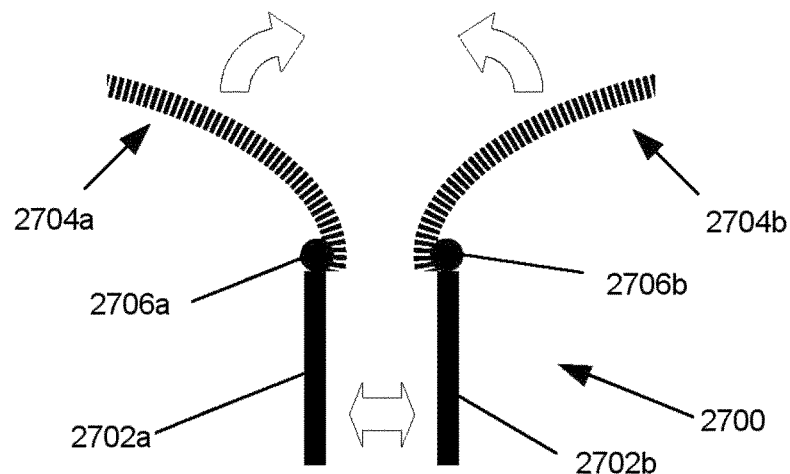
FIGS. 27A and 27B are partial top views of an embodiment of a manipulator in accordance with the present invention in an open and closed configuration, respectively.
Figure 27B:
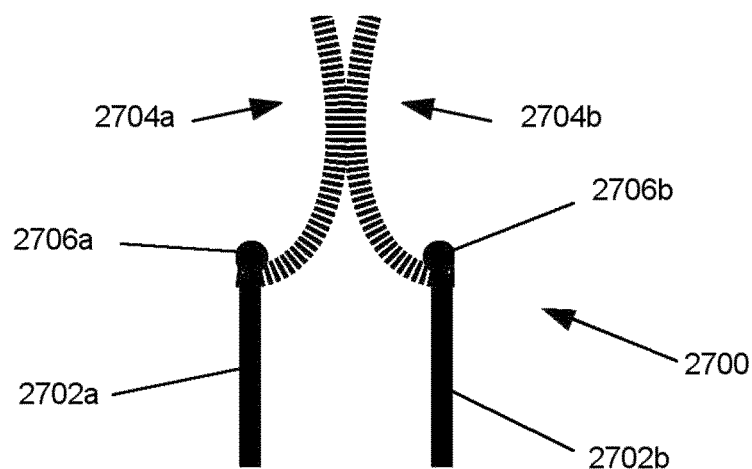
Figure 28A:
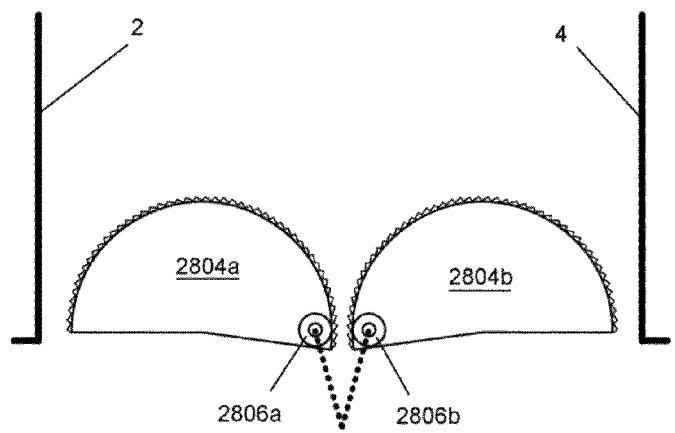
FIGS. 28A-28E illustrate an alternative embodiment of a grasping surface for use as a locomotive device in accordance with the present invention.
Figure 28B:
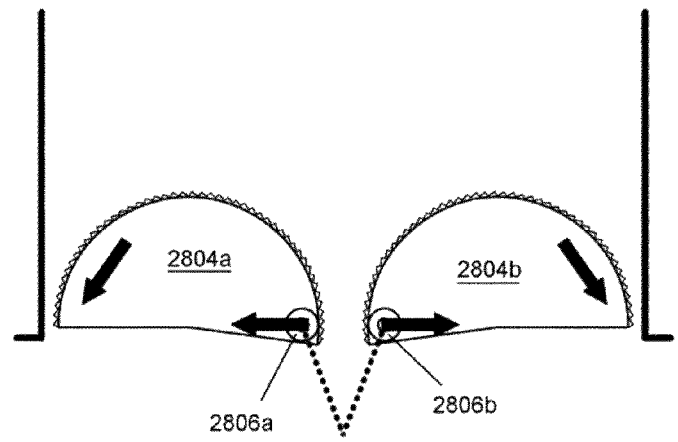
Figure 28C:
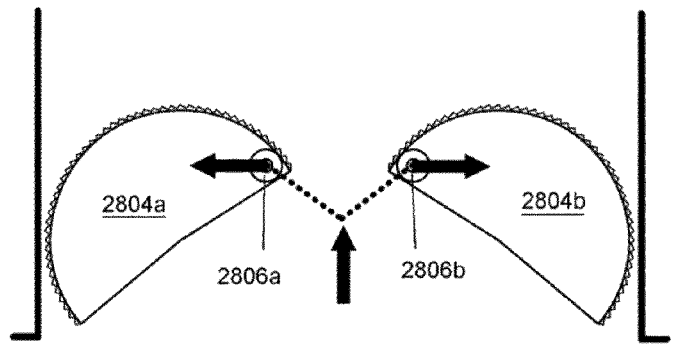
Figure 28D:
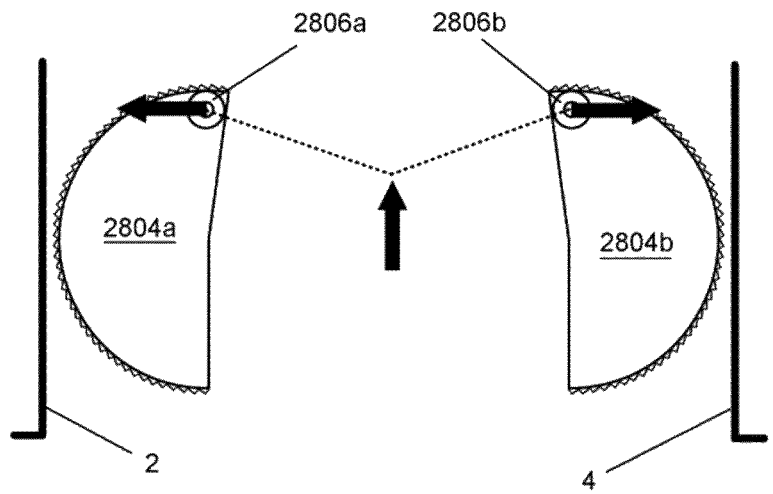
Figure 28E:
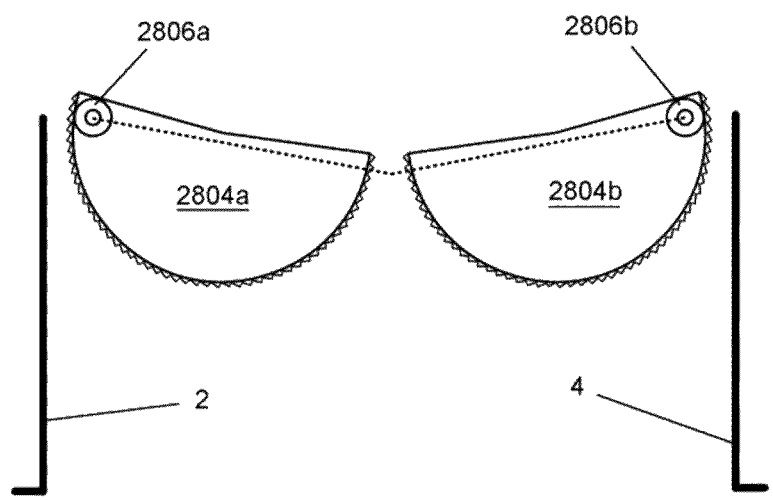

FIGS. 27A and 27B illustrate an embodiment of a manipulator 2700 in accordance with the present invention adapted for pulling in and grasping tissues with large surfaces and mass and adapted for manipulation in deep layers. The static process of grasping is divided into two stages, the first stage including static grapping and the second phase including dynamic pulling in and fixing of the tissue. The grasping surfaces 2704a, 2704b are not actuated by a spring bias, but rather are pivoted by separate mechanics independent, or semi-independent of arm movement. For example, the grasping surfaces 2704a, 2704b can be pivoted by cables, complementary arms, etc. In this embodiment, the grasping surfaces 2704a, 2704b start to rotate while the arms 2702a, 2702b are closed. The arms then begin to open. The manipulator can be useful, for example, in combination with endoscopes, enabling a large quantity of tissue on a large surface to be precisely grasped. The manipulator 2700 comprises a pair of arms 2702a, 2702b each of which is connected with a grasping surface 2704a, 2704b at a pivot point 2706a, 2706b. The grasping surfaces 2704a, 2704b have a semi-parabolic shape that curves outward with a convex orientation relative to respective arms 2702a, 2702b. The arms 2702a, 2702b of the manipulator 2700, as with all of the embodiments of manipulators described herein, can be part of a hand actuated mechanism, for example as a pair of forceps, or alternatively the arms 2702a, 2702b can extend from a robot that can be controlled by a physician or controlled by an automated system.

FIGS. 28A-28E illustrate an embodiment of grasping surfaces 2804a, 2804b for use as a locomotive device, for example to advance an instrument or a more complex device such as a robot. As shown, pivot points 2806a, 2806b of the grasping surfaces 2804a, 2804b are connected with a device (shown schematically as a dotted line). The grasping surfaces 2804a, 2804b grip and advance along walls 2, 4 with the pivot points 2806a, 2806b being drawn forward along the walls 2, 4 (upwards relative to the page). Likewise, the connected device is drawn forward. The grasping surfaces 2804a, 2804b can be useful in myriad different applications, such as introducing instruments, cameras, and tools to an inaccessible disaster site, or moving a cleaning robot into a drain.

Figure 29C:
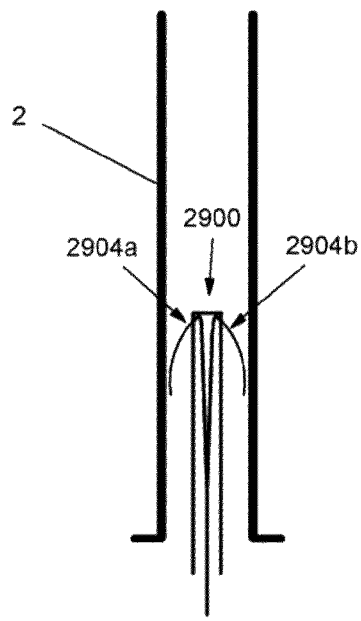
Figure 29C:
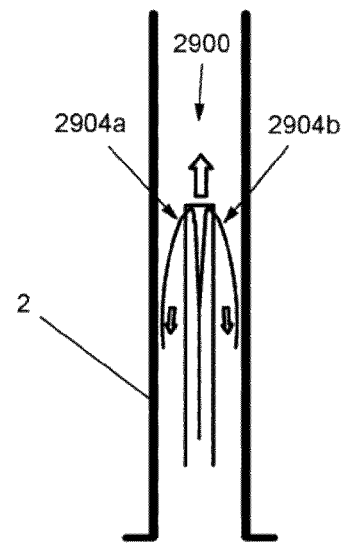
Figure 29C:
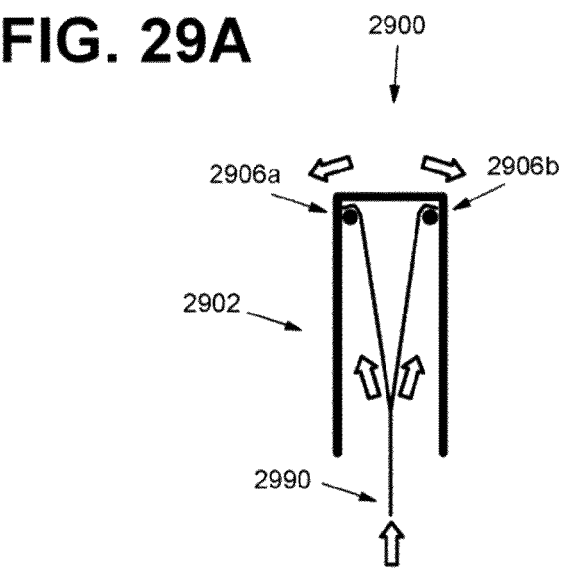

FIGS. 29A-29C illustrate an embodiment of an endoscope 2900 useable, for example, in a bowel or a catheter 2 in an artery. As shown in FIGS. 29A and 29B, the endoscope 2900 is shown being advanced through the catheter 2 (upward along the page) through movement of grasping surfaces in the form of plates 2904a, 2904b. FIG. 29C illustrates the head 2902 of the endoscope 2900. The moving mechanism is a cable 2990 which splits near the end of the head 2902 of the endoscope 2900 to connect to two or more (two as shown) patterned or toothed plates 2904a, 2904b. The plates 2904a, 2904b turn back at pivot points 2906a, 2906b at the end of the head 2902 of the endoscope 2900 and grip the walls of the catheter 2. Advancing the cable 2990, the plates 2904a, 2904b moves backward, advancing the endoscope 2900. This advancement can be limited to a length of the plates 2904a, 2904b and/or cable 2990; however, the advancement can assist in moving the endoscope 2900 when the endoscope 2900 cannot be advanced by pushing the endoscope 2900 along the catheter 2.

Figure 30A:
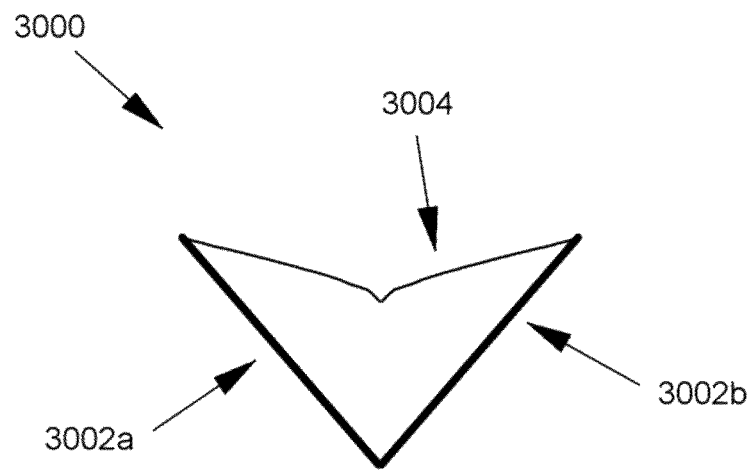
FIGS. 30A and 30B illustrate an alternative embodiment of a grasping surface in accordance with the present invention in an open and closed configuration.
Figure 30B:
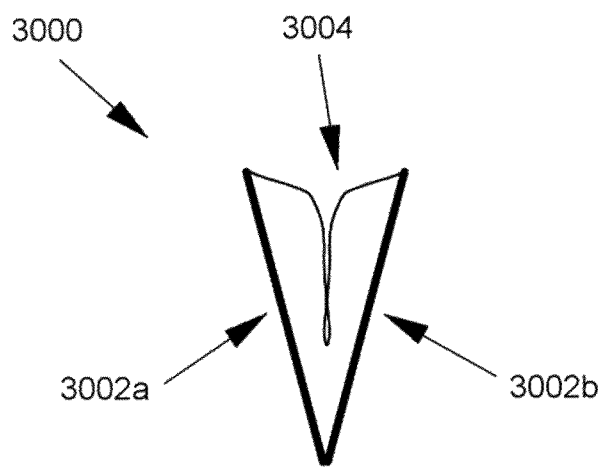

FIG. 30 is a top view a still further embodiment of a head 3000 for use with manipulators in accordance with the present invention. The arms 3002a, 3002b resemble a clip, connecting at a proximal end. A patterned plate 3004 having a "V" shape that acts as grasping surfaces is connected with a distal end of the arms 3002a, 3002b. As the distal ends of the arms 3002a, 3002b are urged together, the grasping surfaces of the plate 3004 grab, pulls in, and fixes a target between the arms 3002a, 3002b.

In certain embodiments described herein, application fields for the invention include, but are not limited to, grasping of tissues in locations difficult to access and movement within and manipulation of tubes and other walled structures. However, upon reflecting on the teachings contained herein, one of ordinary skill in the art will appreciate the myriad different applications and variations of actuatable grasping surfaces, all of which are intended to fall within the scope of the invention.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

The invention claimed is:

1. A manipulator adapted to grasp and draw tissue comprising:
   a first arm having a distal end and a proximal end;
   a second arm having a distal end and a proximal end;
   wherein the distal ends of the first and second arm are separated by a distance;
   a first grasping surface connected to and extending from the distal end of the first arm at a first pivot point;
   wherein the first grasping surface is rigid and cylindrical in shape;
   a second grasping surface connected to and extending from the distal end of the second arm at a second pivot point;
   wherein the second grasping surface is rigid and cylindrical in shape;
   wherein the first grasping surface and the second grasping surface are biased toward each other;
   wherein when the first arm and second arm are actuated to reduce the distance, the manipulator is adapted such that tissue, configured to be arranged between the first grasping surface and the second grasping surface, resists actuation of the first arm and the second arm; and
   wherein the first arm and second arm are further actuatable so that the first grasping surface and the second grasping surface pivot at respective first and second pivot points such that the distance between the distal ends of the first and second arms is reduced; and
   the manipulator is adapted such that tissue is configured to be drawn toward the proximal end of the first and second arms;
   wherein the entire first grasping surface and the entire second grasping surface are offset from a plane defined by the first arm and the second arm in order to avoid interference with said first and second arms, as the first and second arms are activated to reduce the distance; and
   wherein the first grasping surface is provided on a first disk and the second grasping surface is provided on a second disk.

2. The manipulator of claim 1 wherein:
   the first pivot point for the first grasping surface is off-center and near a first edge of the first disk and near the first grasping surface; and
   the second pivot point for the second grasping surface is off-center and near a second edge of the second disk and near the second grasping surface.

3. The manipulator of claim 1 wherein:
   said first grasping surface is biased toward the second grasping surface by a first spring force; and
   said second grasping surface is biased toward the first grasping surface by a second spring force.

4. The manipulator of claim 1 wherein the cylindrical shape of the first grasping surface is elliptical and wherein the cylindrical shape of the second grasping surface is elliptical.

5. The manipulator of claim 1 wherein the first disk is a first partial disk and wherein the second disk is a second partial disk.

* * * * *